US006974877B2

(12) United States Patent
Vogel et al.

(10) Patent No.: US 6,974,877 B2
(45) Date of Patent: Dec. 13, 2005

(54) PROCESS FOR PREPARING PENTACENE DERIVATIVES

(75) Inventors: Dennis E. Vogel, Lake Elmo, MN (US); Kim M. Vogel, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 223 days.

(21) Appl. No.: 10/256,489

(22) Filed: Sep. 27, 2002

(65) Prior Publication Data

US 2003/0100779 A1 May 29, 2003

Related U.S. Application Data

(63) Continuation-in-part of application No. 09/966,954, filed on Sep. 27, 2001, now abandoned.

(51) Int. Cl.$^7$ ............................ C07C 50/16; C07C 41/00

(52) U.S. Cl. ....................... 552/271; 540/145; 568/633; 568/300; 568/68; 570/183; 257/40

(58) Field of Search .......................... 552/271; 568/633; 568/300, 68; 570/183; 257/40

(56) References Cited

U.S. PATENT DOCUMENTS

| | | | |
|---|---|---|---|
| 3,627,655 A | 12/1971 | Perez-Albuerne | |
| 5,707,779 A | 1/1998 | Naito | |
| 6,165,383 A | 12/2000 | Chou | |
| 6,465,116 B1 | 10/2002 | Ishikawa et al. | |
| 6,489,046 B1 * | 12/2002 | Ikeda et al. | 428/690 |

FOREIGN PATENT DOCUMENTS

| | | |
|---|---|---|
| EP | 0 726 304 A2 | 8/1996 |
| EP | 0 786 820 A2 | 7/1997 |
| JP | 63-199759 | 8/1988 |
| JP | 11-354277 | 12/1999 |
| WO | WO 00/03565 | 1/2000 |
| WO | WO 00/56933 | 9/2000 |
| WO | 01/45469 * | 6/2001 |
| WO | WO 01/45469 A1 | 6/2001 |
| WO | WO 03/016599 A1 | 2/2003 |

OTHER PUBLICATIONS

Machek, Guido, AN 24:46489, CA, Monatsh. (1930), 56, 116–34 (Full reference is also enclosed along with English abstract.*
Philippi, Ernst et al, AN 17:11407 CA, Monatsh. (1923), 43, 615–9, 621–31. (Full reference is also enclosed along with English abstract).*
B. Hulin et al., "A Convenient, Mild Method for the Cyclization of 3– and 4–Arylalkanoic Acids via Their Trifluoromethanesulfonic Anhydride Derivatives", J. Org. Chem., vol. 49, (1984), pp. 207–209.

T. Yamato et al., "Organic Reactions Catalyzed by Solid Superacids. 5.$^1$ Perfluorinated Sulfonic Acid Resin (Nafion–H) Catalyzed Intramolecular Friedel–Crafts Acylation", J. Org. Chem., vol. 56, No. 12, (1991), pp. 3955–3957.

V. Premasagar et al., "Methanesulfonic Acid Catalyzed Cyclization of 3–Arylpropanoic and 4–Arylbutanoic Acids to 1–Indanones and 1–Tetralones", J. Org. Chem., vol. 46, No. 14, (1981), pp. 2974–2976.

Mills and Mills: The Synthetical Production of Derivatives of Dinaphthanthracene "CCXXX.—The Synthetical Production of Derivatives of Dinaphthanthracene", J. Chem. Soc., vol. 101, (1912), pp. 2194–2208.

J. M. Shaw et al., "Organic Electronics: Introduction", IBM J. Res. & Dev., vol. 45, No. 1, (Jan. 2001), pp. 3–9.

C. D. Dimitrakopoulos et al., "Organic Thin–Film Transistors: A Review of Recent Advances", IBM J. Res. & Dev., vol. 45, No. 1, (Jan. 2001), pp. 11–27.

C. D. Dimitrakopoulos et al., "Molecular Beam Deposited Thin Films of Pentacene for Organic Field Effect Transistor Applications", J. Appl. Phys., vol. 80, No. 4, (Aug. 15, 1996), pp. 2501–2508.

D. J. Gundlach et al., "Solvent–Induced Phase Transition in Thermally Evaporated Pentacene Films", Appl. Phys. Lett., vol. 74, No. 22, (May 31, 1999), pp. 3302–3304.

(Continued)

Primary Examiner—S. Qazi
(74) Attorney, Agent, or Firm—Lisa P. Fulton

(57) ABSTRACT

A process for preparing substituted pentacene compounds comprises the step of cyclizing substituted bis(benzyl) phthalic acids using an acid composition comprising trifluoromethanesulfonic acid, the substituted bis(benzyl) phthalic acids being represented by the following general formulas:

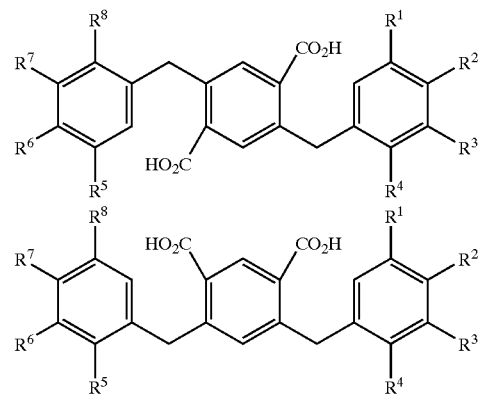

wherein each R (that is, each of the groups $R^1$ through $R^8$) is independently an electron-donating group, a halogen atom, a hydrogen atom, or a combination thereof.

20 Claims, No Drawings

OTHER PUBLICATIONS

Y.-Y. Lin et al., "Stacked Pentacene Layer Organic Thin–Film Transistors with Improved Characteristics" IEEE Electron Device Letters, vol. 18, No. 12, (Dec. 1997), pp. 606–608.

A. Orita et al., "Integrated Chemical Process: One–Pot Aromatization of Cyclic Enones by the Double Elimination Methodology" Angew. Chem. Int. Ed., vol. 38, No. 15, (1999) pp. 2267–2270.

A. R. Wartini et al., "Intramolecular Electron Transfer Between Terminal 1,4–Dimethoxybenzene Units in Radical Cations with a [2.2](1,4)Naphthalenophane, [2.2](1,4)Anthracenophane, and Pentacene Skeleton", Eur. J. Org. Chem., (1998), pp. 1161–1170.

Kirk–Othmer Enc. Of Chemical Technology, "Friedel–Crafts Reactions", vol. 11, 4$^{th}$ ed., John Wiley & Sons, Inc., NY, (1994), pp. 1043–1075.

E. Philippi et al., "Dinaphthanthracene Series V, VI", Monatshefte Fur Chemie, vol. 43, (1923), pp. 615–619.

E. Philippi, "Synthesis of Linear Diphthaloyl Benzene", Monatshefte Fur Chemie, vol. 32, (1911), pp. 631–635.

E. Philippi, "Condensation of Pyromellitic Anhydride with Benzene and Toluene", Monatshefte Fur Chemie, vol. 34, (1913), pp. 705–715.

E. Philippi et al., "Dinaphthanthracene Series IV Bromo Derivatives", Monatshefte Fur Chemie, vol. 42, (1921), pp. 1–4.

G. Machek, "Linear Pentacene Serie XIX Constitution of the Bi–derivatives of 5,7,12,14–Pentacenediquinone", Monatshefte Fur Chemie, vol. 56, (1930), pp. 116–134.

H. E. Katz et al., "Synthetic Chemistry for Ultrapure, Processable, and High–Mobility Organic Transistor Semiconductors", American Chemical Society, Accounts of Chemical Research, vol. 34, No. 5, (2001), pp. 359–369.

S. M. Sze, Physics of Semiconductor Devices, MOSFET Structures, 8.5.6 Thin–Film Transistor, 2$^{nd}$ ed., John Wiley & Sons, (1981), pp. 492–493.

S. M. Sze, Physics of Semiconductor Devices, MOSFET Basic Device Characteristics, 8.2.2 Linear and Saturation Regions, 2$^{nd}$ ed., John Wiley & Sons, (1981), pp. 438–442.

J. M. Allen et al., "Friedel–Crafts Cyclisation–VI[1] Polyphosphoric Acid–Catalysed Reactions of Crotonophenones and Chalcones", Tetrahedon, vol. 33, (1977), pp. 2083–2087.

H. de Diesbach et al. "Derivatives of Dinaphthanthracene Diquinone and the Synthesis of Dinaphthaleneanthracene Diquinone", Helvetica Chim. Acta, vol. 7, (1924), pp. 644–653.

E. Clar et al., "Information on Polycyclic Aromatic Hydrocarbons and Their Derivatives, V. Naphthoanthracene, Their Oxidation Products and a New Class of Deep–Colored Hydrocarbons", Chem Berichte, (1929), 3027–3032.

E. Clar et al., "Information on Polycyclic Aromatic Hydrocarbons and Their Derivatives, II. [Naphtho–2',3':1,2–anthracene][1]). Its Homologues and its Oxidation Products", Chem Berichte, (1929). p. 940–947.

E. Clar et al., "Information on Polycyclic Aromatic Hydrocarbons and Their Derivatives, VIII. [Naphtho–2',3':1,2–anthracene],[2,3:6,7–dibenzoanthracenes–9,10–diyls] and Their Oxidation Products", Chem Berichte, (1929), p. 981–986.

F. Effenberger et al., "Catalytic Friedel–Crafts Acylation of Aromatic Compounds", Angew. Chem. Internat. Edit., vol. 11, No. 4 (1972), pp. 300–301.

G. A. Olah et al., "Nafion–H Catalysed Intramolecular Friedel–Crafts Acylation : Formation of Cyclic Ketones and Related Heterocycles", Synlett, No. 7, (1999), pp. 1067–1068.

S. Miki et al., "Synthesis of 1,2,3,–Tri–t–butyl–6,13– and 8,9,10–Tri–t–butyl–5,14–pentacenequinones and Their Photochromic Behaviors: New Photochromic Molecules", Tetrahedron, vol. 52, No. 12, (1996), pp. 4269–4276.

T. Takahashi, et al., "Straightforward Method for Synthesis of Highly Alkyl–Substituted Naphthacene and Pentacene Derivatives by Homologation", J. Am. Chem. Soc., (2000), pp. 12876–12877, vol. 122.

* cited by examiner

PROCESS FOR PREPARING PENTACENE DERIVATIVES

STATEMENT OF PRIORITY

This application is a continuation-in-part of application Ser. No. 09/966,954 filed Sep. 27, 2001, now abandoned, and claims the priority thereof.

FIELD

This invention relates to a process for preparing aromatic organic compounds that are useful as semiconductors. In another aspect, this invention relates to novel compounds that are useful in the preparation of aromatic organic semiconductor compounds.

BACKGROUND

Traditionally, inorganic silicon and gallium arsenide semiconductors, silicon dioxide insulators, and metals such as aluminum and copper have dominated the semiconductor industry. In recent years, however, there has been an increasing research effort in using organic thin-film transistors (OTFTs) as an alternative to the traditional thin-film transistors based on inorganic materials.

Pentacene, thiophene oligomers, and regioregular polythiophenes have been the most widely researched organic semiconductors. Of these classes of semiconducting organic materials, the highest charge-carrier mobility values have been observed for pentacene. Charge-carrier mobility values greater than 1.5 cm$^2$ V$^{-1}$ s$^{-1}$, on/off current ratios greater than 10$^8$, and sub-threshold voltages of less than 1.6 V have been reported for pentacene-based transistors. These values are comparable or superior to those of amorphous silicon-based devices.

However, the performance of pentacene-based devices can be difficult to reproduce. This lack of reproducibility is due to the polymorphic nature of pentacene. The alignment or structural order of the pentacene molecules differs for each polymorph or crystallographic phase, and this structural order determines the electronic properties of the device. The crystallographic phase adopted by pentacene depends on the process and conditions under which the crystals are formed. For example, when pentacene is vapor-deposited onto a substrate, a thin film phase is formed. This thin film phase is more effective at transporting charge than pentacene's bulk or single crystal phase, but it is meta-stable. For example, the thin film form of pentacene can be converted to the bulk phase by exposure to solvents such as isopropanol, acetone or ethanol. (See, for example, Gundlach et al., Applied Physics Letters, 74(22) 3302 (2000).)

In order to achieve maximum performance, pentacene must generally be deposited from the vapor phase by vacuum sublimation. The vacuum sublimation process, however, requires expensive equipment and lengthy pump-down cycles. Solution processing has the potential to greatly reduce the manufacturing costs associated with the use of organic semiconductors. Pentacene, however, is insoluble in common solvents and is therefore not a good candidate for solution processing.

SUMMARY

In view of the foregoing, we recognize that there is a need for organic semiconductors that can provide stable, reproducible electronic performance characteristics, that exhibit charge-carrier mobilities comparable to or better than those of pentacene, and that are preferably at least somewhat more soluble than pentacene in common organic solvents. Furthermore, in order for such compounds to be commercially attractive, we recognize that there is a need for a scaleable and economical process for preparing the compounds.

Briefly, in one aspect, the present invention provides a process for preparing substituted pentacene compounds that are useful as organic semiconductors. The process comprises the step of carrying out intramolecular Friedel-Crafts cyclization of substituted bis(benzyl)phthalic acids using an acid composition comprising trifluoromethanesulfonic acid, the substituted bis(benzyl)phthalic acids being represented by the following general formulas:

Formula I(a)

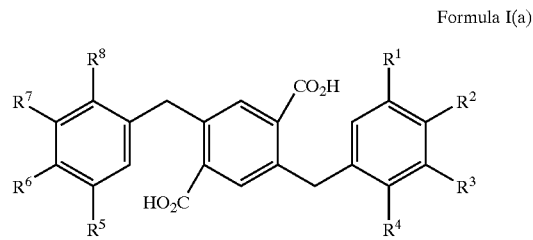

Formula I(b)

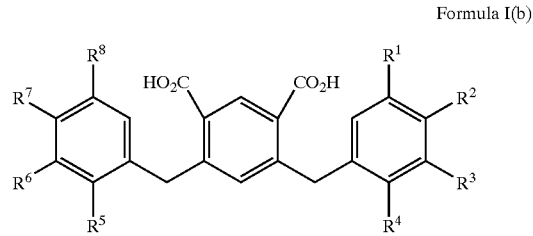

wherein each R (that is, each of the groups R$^1$ through R$^8$) is independently selected from the group consisting of electron-donating substituents (for example, alkyl, alkoxy, or thioalkoxy), halogen atoms, hydrogen atoms, and combinations thereof. As used herein, the term "phthalic acid" refers to terephthalic acid (1,4-benzenedicarboxylic acid) and isophthalic acid (1,3-benzenedicarboxylic acid) collectively.

Intramolecular Friedel-Crafts cyclization reactions of carboxylic acids can generally be accomplished using a strong acid such as concentrated sulfuric acid, fuming sulfuric acid, polyphosphoric acid or anhydrous hydrofluoric acid. However, both the above-described substituted bis(benzyl) phthalic acids and the corresponding substituted is(benzoyl) phthalic acids are usually unreactive under these conditions. It appears that the intramolecular Friedel-Crafts cyclization of these substituted compounds usually cannot be accomplished with the strong acids that are typically used for this type of reaction.

It has been discovered, however, that Friedel-Crafts cyclization of substituted bis(benzyl)phthalic acids to form the corresponding substituted pentacenediones can be accomplished using an acid composition comprising trifluoromethanesulfonic acid. Surprisingly, the cyclization can be carried out at room temperature in many cases. The resulting substituted pentacenedione compounds can then be reduced and dehydrated to the corresponding substituted pentacene compounds. The substituted pentacene compounds provide charge-carrier mobilities comparable to those of pentacene, while also exhibiting improved electronic stability and reproducibility of performance characteristics in a semiconductor device.

The process of the invention meets the need for a scaleable and economical route to the substituted pentacenediones and substituted pentacenes. The process can also be more generally applied to the preparation of diaryl cyclic ketones other than the substituted pentacenediones, if desired.

In other aspects, this invention also provides novel intermediates in the form of the substituted pentacenediones resulting from the intramolecular Friedel-Crafts cyclization reaction, as well as certain substituted bis(benzyl)phthalic acid starting compounds and certain substituted bis(benzoyl) phthalic acid starting compound precursors.

In still another aspect, this invention provides a process for preparing acenes comprising the step of treating at least one diarene-annellated cyclohexanone, cyclohexa-1,2-dione, or cyclohexa-1,4-dione (for example, an anthrone or a quinone) with aluminum alkoxide. As used herein, the term "diarene-annellated" in reference to a cyclic ketone means having two arenes, each of which is fused to the ring of the cyclic ketone, and each of which may further contain one or more additional cyclic ketone moieties.

DETAILED DESCRIPTION

The process of the invention for preparing substituted pentacene compounds comprises the step of cyclizing the above-described substituted bis(benzyl)phthalic acids to form the corresponding substituted pentacenediones (that is, substituted 7,14-dihydropentacene-5,12-diones and substituted pentacene-5,7(12H,14H)-diones).

Preparation of Substituted Bis(benzyl)phthalic Acid Starting Compounds

The above-described substituted bis(benzyl)phthalic acid starting compounds can be prepared by first preparing the corresponding substituted bis(benzoyl)phthalic acids and then reducing them. The substituted bis(benzoyl)phthalic acids can be prepared by combining at least one substituted benzene with pyromellitic dianhydride (benzene-1,2,4,5-tetracarboxylic acid dianhydride) or a derivative thereof (for example, dimethyl 2,5-bis(chlorocarbonyl)terephthalate) in the presence of a Lewis acid (for example, $AlCl_3$), as can be represented by the following general scheme:

Reaction Scheme A

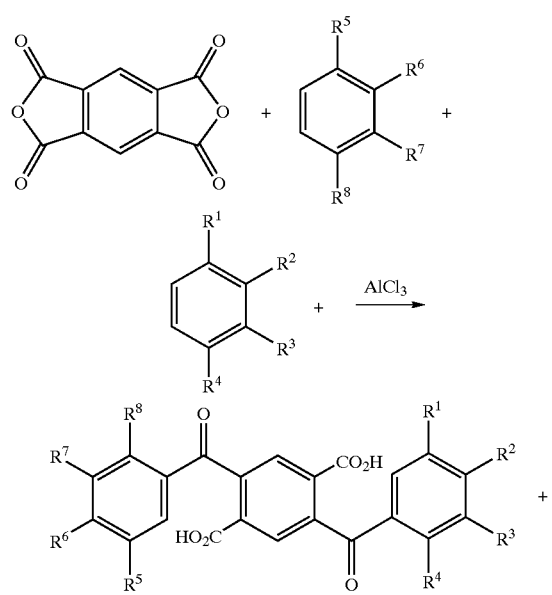
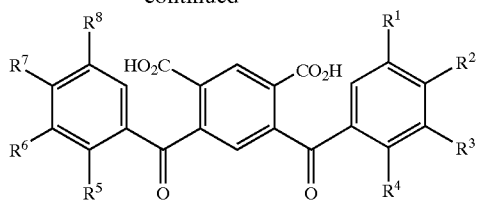

wherein each R (that is, each of the groups $R^1$ through $R^8$) is independently selected from the group consisting of electron-donating groups, halogen atoms, hydrogen atoms, and combinations thereof. As used herein, the term "combinations" of substituents includes, monovalent combinations (for example, a bromomethyl substituent)as well as substituents formed by the bonding together of the substituents on two adjacent carbon atoms to form a ring structure (for example, two alkyl substituents on adjacent carbon atoms can be bonded together to form a divalent alkylene group that bridges or links the carbon atoms).

Preferably, each R is independently selected from the group consisting of alkyl groups, alkoxy groups, thioalkoxy groups, halogen atoms, hydrogen atoms, and combinations thereof. More preferably, each R is independently selected from the group consisting of alkyl groups, alkoxy groups, hydrogen atoms, and combinations thereof. Even more preferably, each R is independently selected from the group consisting of alkyl groups and hydrogen atoms. Most preferably, each R is independently selected from the group consisting of methyl, n-hexyl, n-nonyl, n-dodecyl, sec-butyl, 3,5,5-trimethylhexyl, 2-ethylhexyl, and hydrogen.

Preferably, only $R^2$ and $R^6$ of the substituted bis(benzoyl) terephthalic acids (or $R^2$ and $R^7$ of the substituted bis (benzoyl)isophthalic acids) are moieties other than hydrogen. That is, preferably, $R^2$ and $R^6$ of the substituted bis(benzoyl)terephthalic acids (or $R^2$ and $R^7$ of the substituted bis(benzoyl)isophthalic acids) are independently selected from the group consisting of electron-donating groups, halogen atoms, and combinations thereof, and $R^1$, $R^3$, $R^4$, $R^5$, $R^7$, and $R^8$ of the substituted bis(benzoyl) terephthalic acids (or $R^1$, $R^3$, $R^4$, $R^5$, $R^6$, and $R^8$ of the substituted bis(benzoyl)isophthalic acids) are hydrogen.

More preferably, said $R^2$ and $R^6$ (or said $R^2$ and $R^7$) are independently selected from the group consisting of alkyl groups, alkoxy groups, thioalkoxy groups, halogen atoms, and combinations thereof, and said $R^1$, $R^3$, $R^4$, $R^5$, $R^7$, and $R^8$ (or said $R^1$, $R^3$, $R^4$, $R^5$, $R^6$, and $R^8$) are hydrogen.

Still more preferably, said $R^2$ and $R^6$ (or said $R^2$ and $R^7$) are independently selected from the group consisting of alkyl groups, alkoxy groups, and combinations thereof, and said $R^1$, $R^3$, $R^4$, $R^5$, $R^7$, and $R^8$ (or said $R^1$, $R^3$, $R^4$, $R^5$, $R^6$, and $R^8$) are hydrogen.

Even more preferably, said $R^2$ and $R^6$ (or said $R^2$ and $R^7$) are independently alkyl, and said $R^1$, $R^3$, $R^4$, $R^5$, $R^7$, and $R^8$ (or said $R^1$, $R^3$, $R^4$, $R^5$, $R^6$, and $R^8$) are hydrogen.

Most preferably, said $R^2$ and $R^6$ (or said $R^2$ and $R^7$) are independently selected from the group consisting of methyl n-hexyl n-nonyl n-dodecyl sec-butyl, 3,5,5-trimethylhexyl, and 2-ethylhexyl, and said $R^1$, $R^3$, $R^4$, $R^5$, $R^7$, and $R^8$ (or said $R^1$, $R^3$, $R^4$, $R^5$, $R^6$, and $R^8$) are hydrogen.

Reactions of this type (electrophilic aromatic substitution reactions) are well known in organic chemistry and have been described, for example, by Henri de Diesbach and Victor Schmidt in Helv. Chim. Acta 7, 648 (1924); by William Hobson Mills and Mildred Mills in J. Chem. Soc. 101, 2200 (1912); by Ernst Philippi in Monatshefte fur Chemie 32, 634 (1911); by Ernst Philippi and Reinhard Seka in Monatshefte fur Chemie 43, 615 (1922); by Ernst Philippi and Fedora Auslaender in Monatshefte fur Chemie 42, 1 (1921); and by Guido Machek in Monatshefte fur Chemie 56, 130 (1930).

Preferably, the reaction is carried out in the presence of an inert solvent and an amine base in order to keep the reaction mixture fluid and to decrease the amount of rearrangement of the substituents on the aromatic ring during the reaction. Examples of useful inert solvents include 1,2-dichloroethane, dichlorobenzene, dichloromethane, carbon disulfide, nitrobenzene, and nitromethane. Examples of useful amine bases include tertiary amines such as triethylamine, diisopropylethylamine, and 1,4-diazabicyclo[2.2.2]octane (DABCO). If desired, the reaction mixture can be agitated and/or heated.

Suitable substituted benzenes can be represented by the following formula:

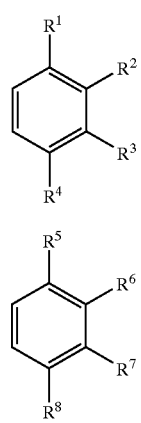

Formula II(a)

Formula II(b)

wherein each R (that is, each of the groups $R^1$ through $R^8$) is independently selected from the group consisting of electron-donating groups, halogen atoms, hydrogen atoms, and combinations thereof.

Preferably, each R is independently selected from the group consisting of alkyl groups, alkoxy groups, thioalkoxy groups, halogen atoms, hydrogen atoms, and combinations thereof. More preferably, each R is independently selected from the group consisting of alkyl groups, alkoxy groups, hydrogen atoms, and combinations thereof. Even more preferably, each R is independently selected from the group consisting of alkyl groups and hydrogen atoms. Most preferably, each R is independently selected from the group consisting of methyl, n-hexyl, n-nonyl, n-dodecyl, sec-butyl, 3,5,5-trimethylhexyl, 2-ethylhexyl, and hydrogen.

Representative examples of substituted benzenes that can be used to prepare the substituted bis(benzoyl)phthalic acids include mono- and dialkoxybenzenes; mono- and dithioalkoxybenzenes; mono- and dihalobenzenes; and mono-, di-, tri-, and tetraalkylbenzenes (for example, toluene, hexylbenzene, nonylbenzene, dodecylbenzene, sec-butylbenzene, p-xylene, 1,2,3,4-tetrahydronaphthalene, and 1,2,3,4-tetramethylbenzene, 3,5,5-trimethylhexylbenzene, and 2-ethylhexylbenzene).

Examples of substituted bis(benzoyl)phthalic acids that can be prepared by the Friedel-Crafts reaction of the above-described substituted benzenes with pyromellitic dianhydride (or a derivative thereof) include:

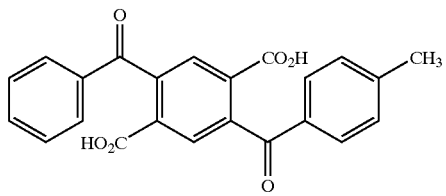

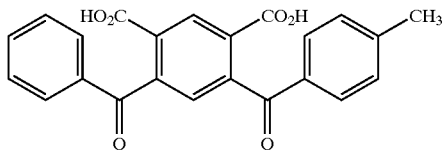

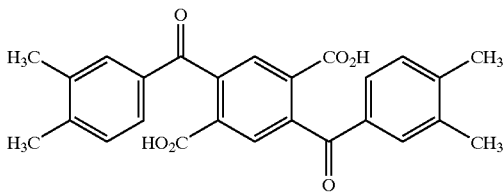

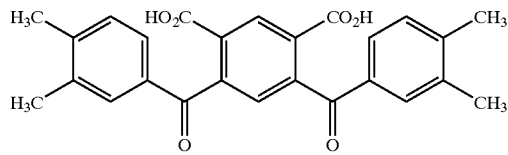

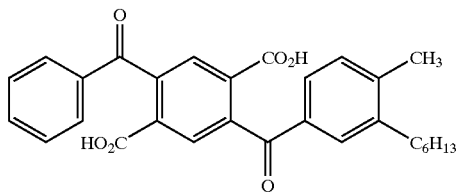

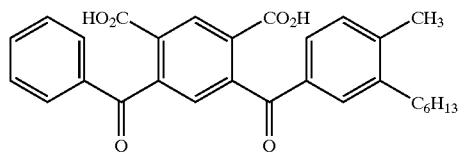

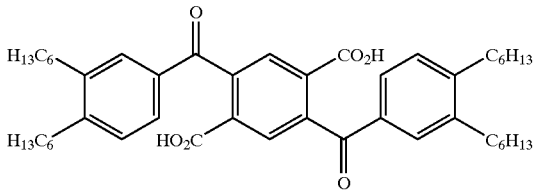

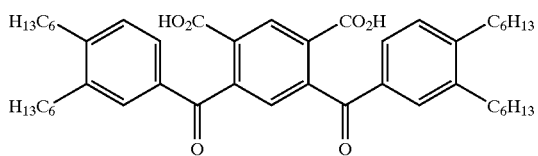

-continued
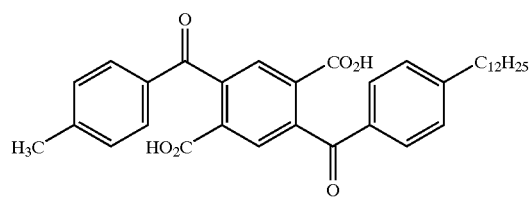
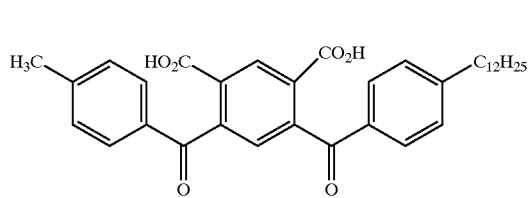
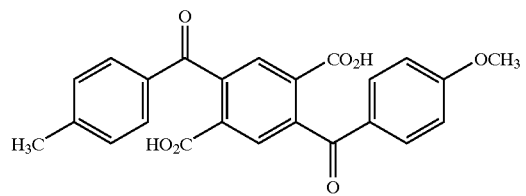
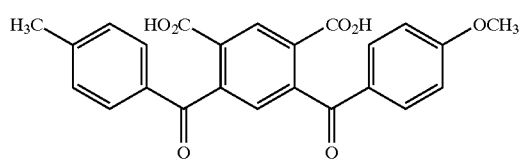
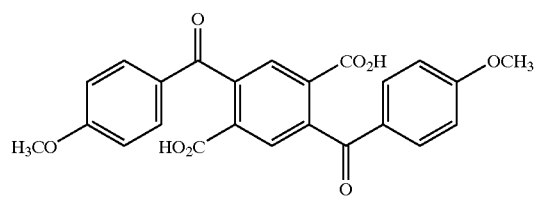
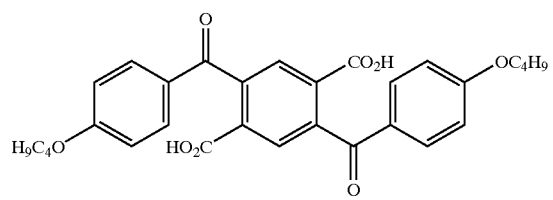
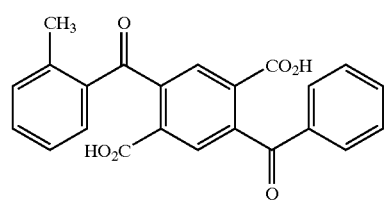
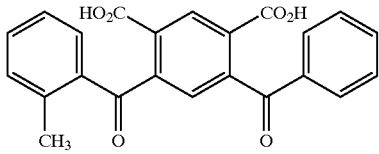
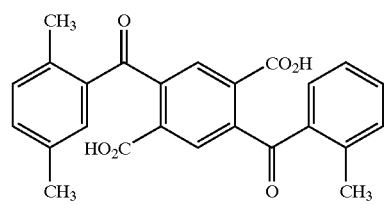
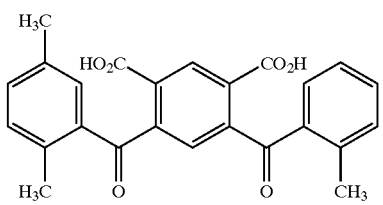
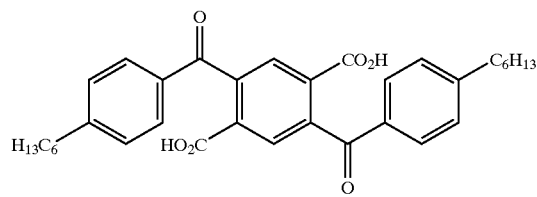
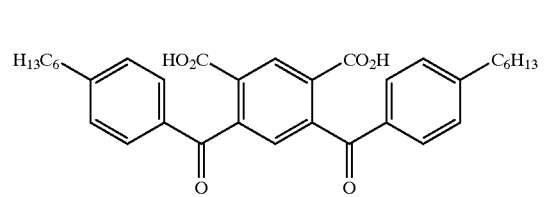
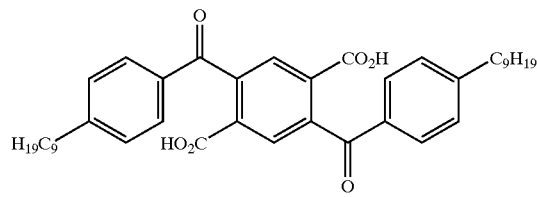
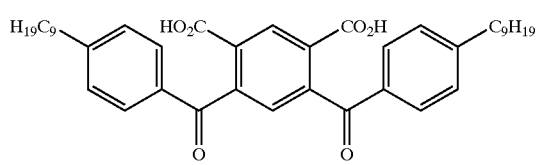
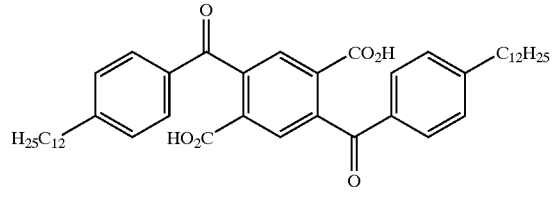
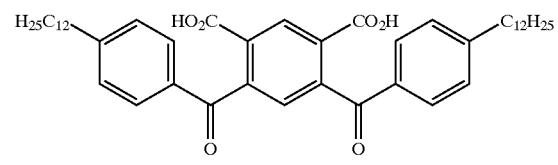

-continued
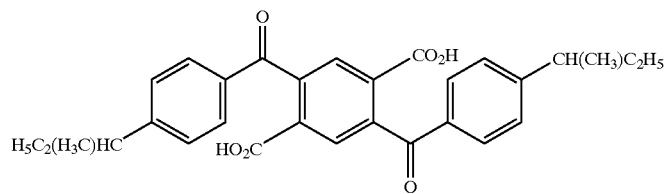
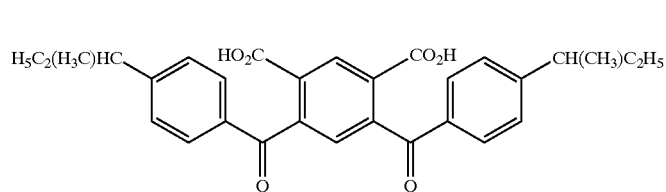
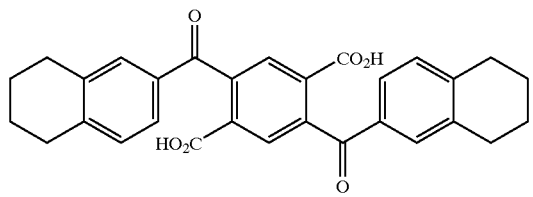
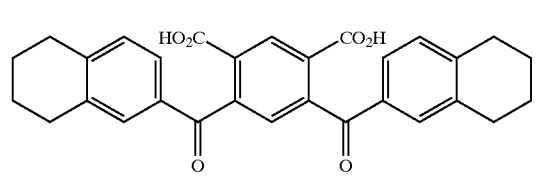
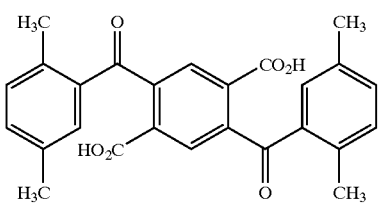
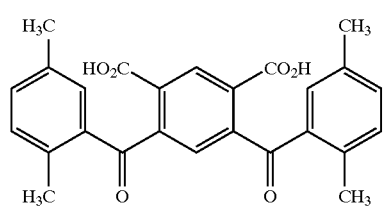
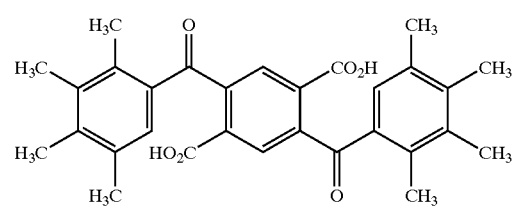
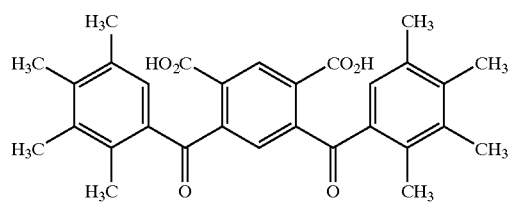
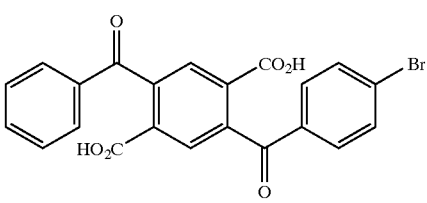
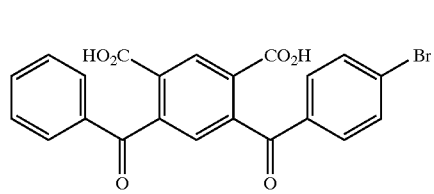
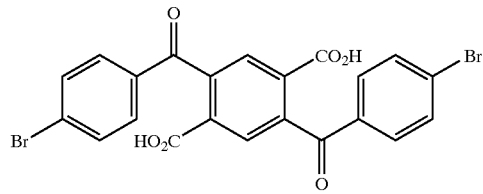
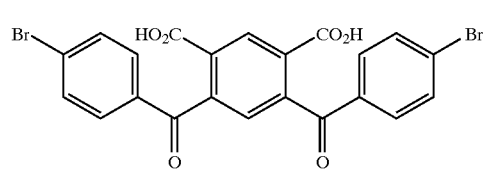
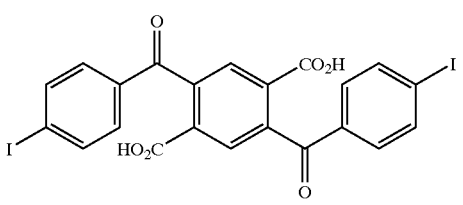
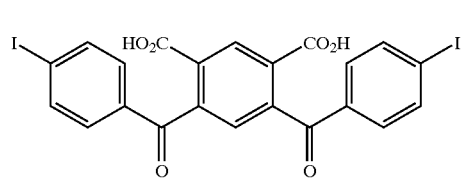
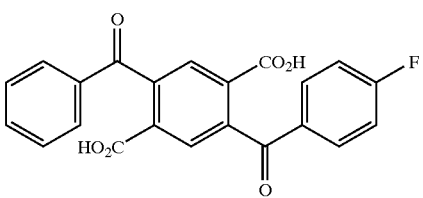

-continued
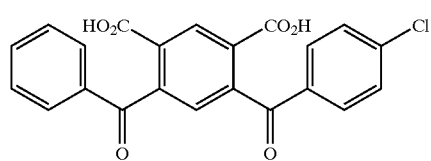
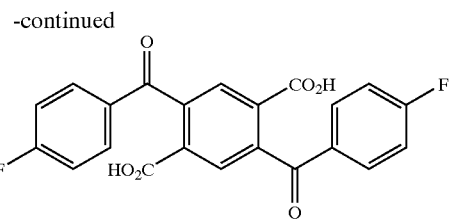
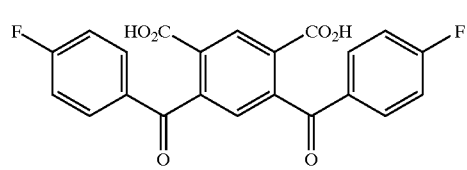
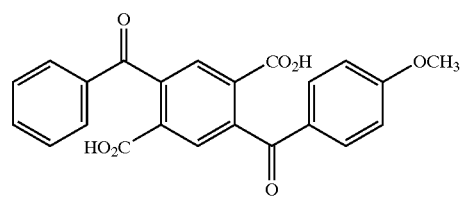
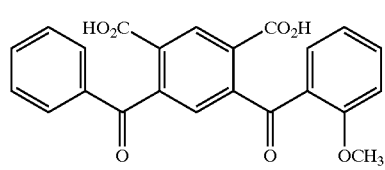
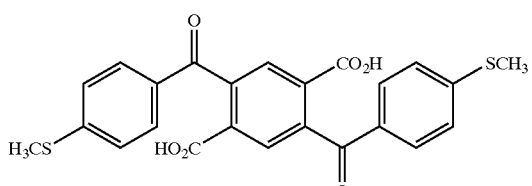
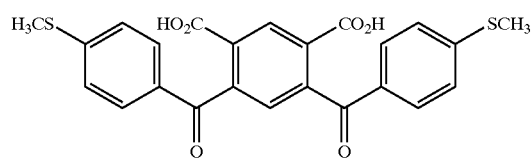
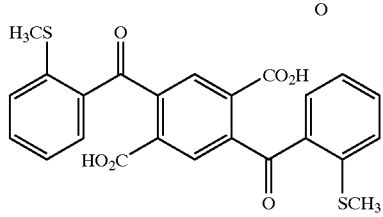
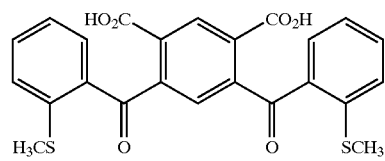
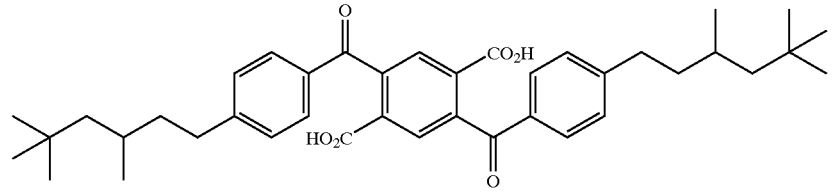
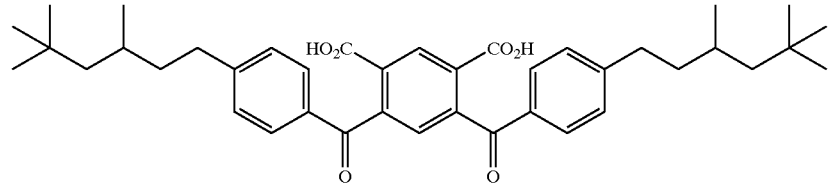
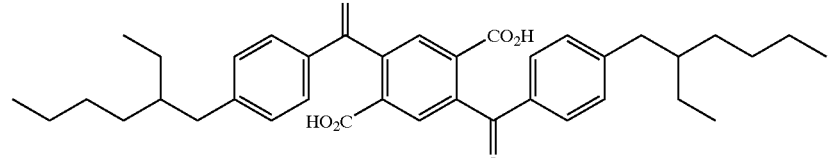
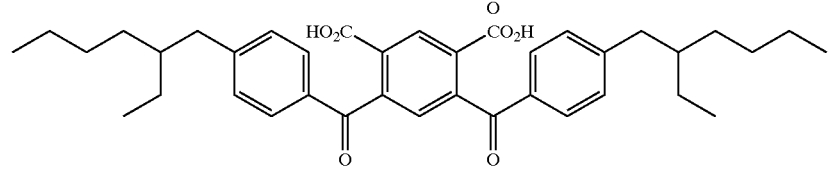

A novel class of the substituted bis(benzoyl)phthalic acid compounds can be represented by the following general formulas:

Formula III(a)

Formula III(b)

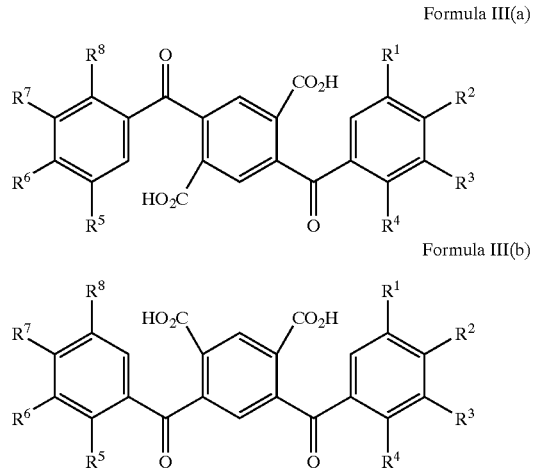

wherein each R (that is, each of the groups $R^1$ through $R^8$) is independently selected from the group consisting of hydrogen atoms and alkyl groups having at least two carbon atoms. Preferably, each R is independently selected from the group consisting of n-hexyl, n-nonyl groups, n-dodecyl groups, sec-butyl, 3,5,5-trimethylhexyl, 2-ethylhexyl, and hydrogen.

Preferably, only $R^2$ and $R^6$ of the substituted bis(benzoyl) terephthalic acids (or $R^2$ and $R^7$ of the substituted bis(benzoyl)isophthalic acids) are moieties other than hydrogen. That is, preferably, $R^2$ and $R^6$ of the substituted bis(benzoyl)terephthalic acids (or $R^2$ and $R^7$ of the substituted bis(benzoyl)isophthalic acids) are independently alkyl groups having at least two carbon atoms, and $R^1$, $R^3$, $R^4$, $R^5$, $R^7$, and $R^8$ of the substituted bis(benzoyl)terephthalic acids (or $R^1$, $R^3$, $R^4$, $R^5$, $R^6$, and $R^8$ of the substituted bis(benzoyl) isophthalic acids) are hydrogen. More preferably, said $R^2$ and $R^6$ (or said $R^2$ and $R^7$) are independently selected from the group consisting of n-hexyl groups, n-nonyl groups, n-dodecyl groups, and sec-butyl groups, 3,5,5-trimethylhexyl groups, 2-ethylhexyl groups, and said $R^1$, $R^3$, $R^4$, $R^5$, $R^7$, and $R^8$ (or said $R^1$, $R^3$, $R^4$, $R^5$, $R^6$, and $R^8$) are hydrogen.

Alternatively, the substituted bis(benzoyl)phthalic acids can be prepared by reaction of pyromellitic dianhydride (or a derivative thereof with) a substituted aromatic organometallic reagent (for example, an aryl magnesium halide or an aryl lithium compound).

The resulting substituted bis(benzoyl)phthalic acids can be reduced to the corresponding substituted bis(benzyl) phthalic acids via reduction methods known in the art. For example, the reduction can be accomplished by using either zinc and aqueous ammonium hydroxide (preferably, with agitation) or catalytic hydrogenation with, for example, palladium or platinum on carbon at, for example, about 2 to 3 atmospheres (preferably, by catalytic hydrogenation; more preferably, by catalytic hydrogenation with palladium on carbon) as shown, for example, below:

Reaction Scheme B

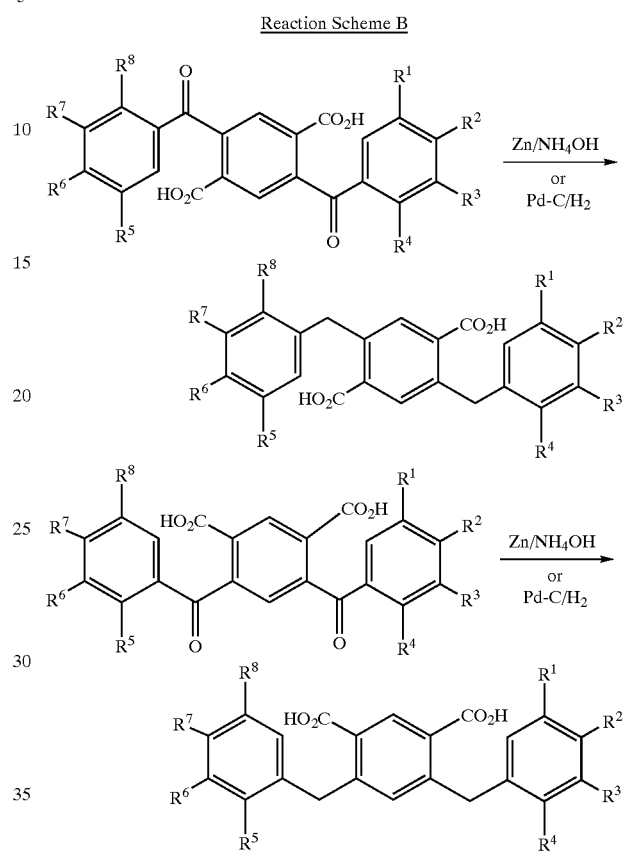

wherein each R (that is, each of the groups $R^1$ through $R^8$) is as defined above for Reaction Scheme A (where the preferences stated for the substituted bis(benzoyl) terephthalic acids also correspond to preferences for the substituted bis(benzyl)terephthalic acids (and the preferences stated for the substituted bis(benzoyl)isophthalic acids also correspond to preferences for the substituted bis (benzyl)isophthalic acids)).

If desired, the substituted bis(benzoyl)terephthalic acids can be separated from the substituted is(benzoyl)isophthalic acids by methods commonly used in the art (for example, by recrystallization, trituration, or chromatography) before the reduction reaction is carried out (or, alternatively, the resulting substituted bis(benzyl)phthalic acid isomers can be separated therafter).

Examples of substituted bis(benzyl)phthalic acids that can be prepared by reduction of substituted bis(benzoyl)phthalic acids include:

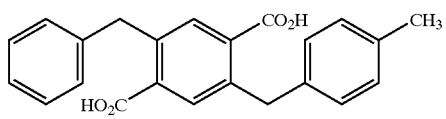
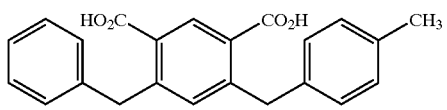

-continued
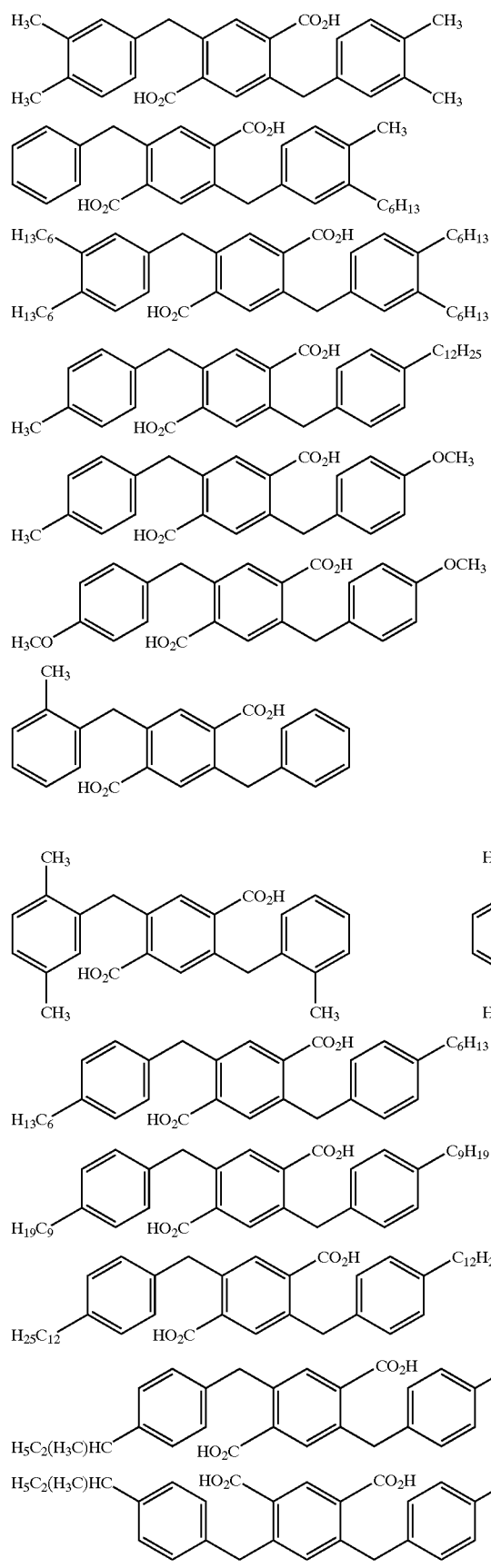
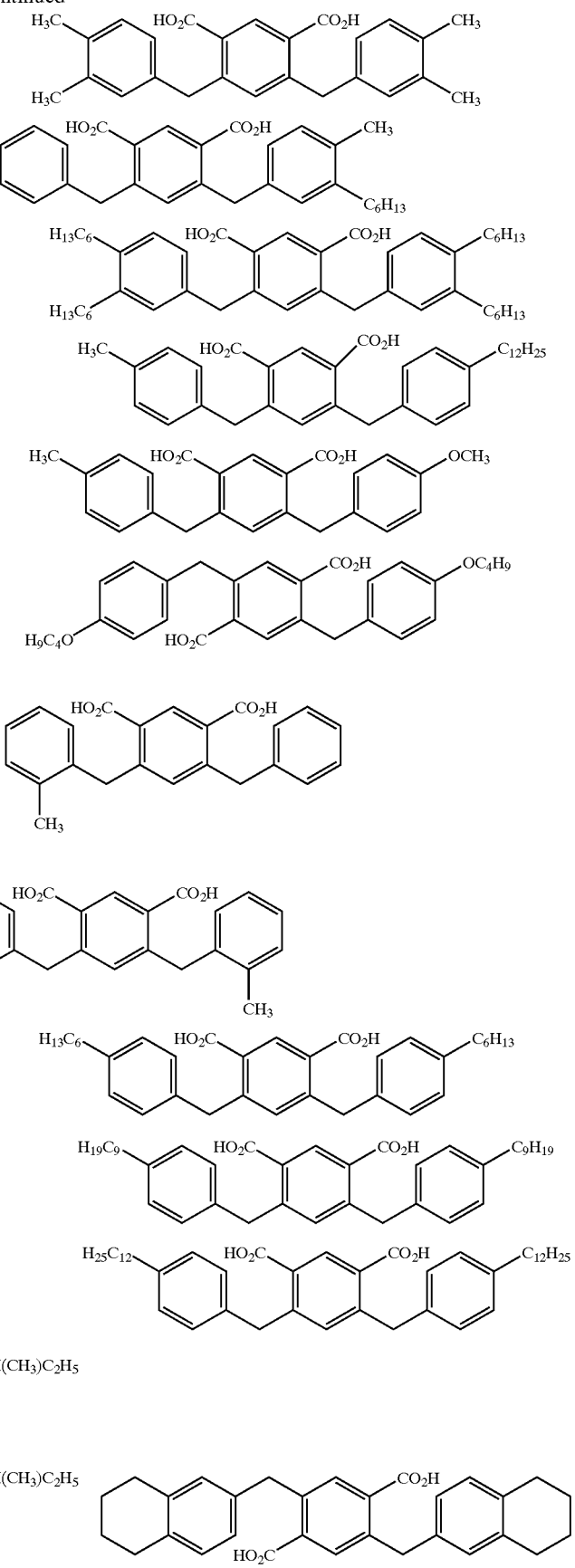

-continued
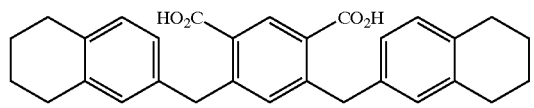
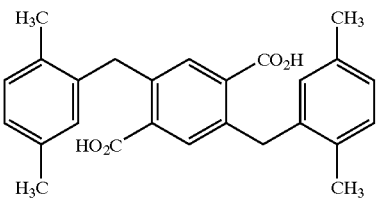
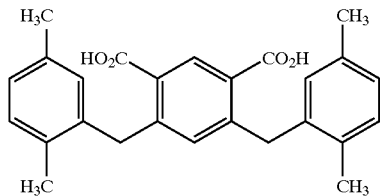
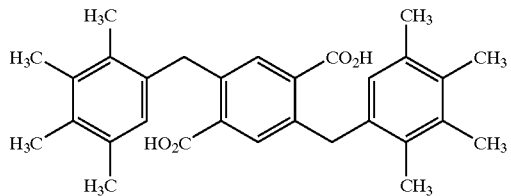
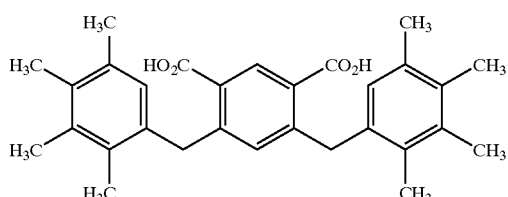
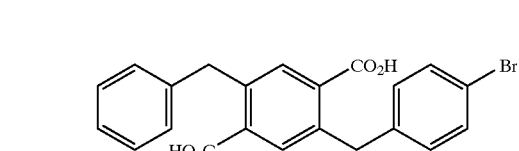
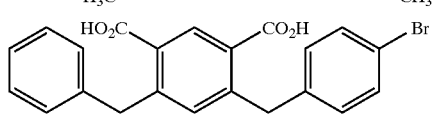
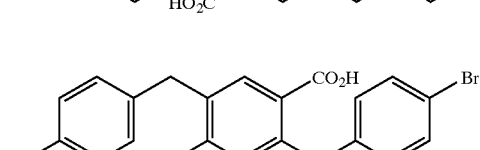
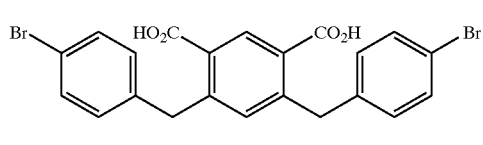
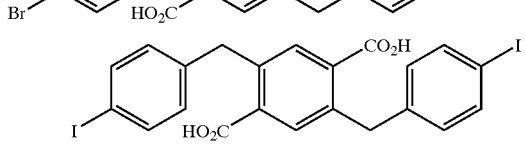
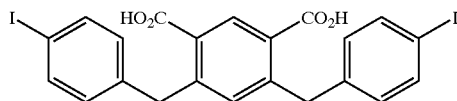
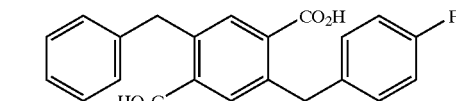
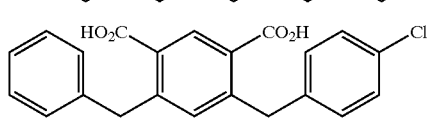
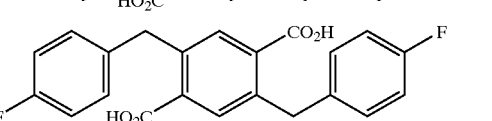
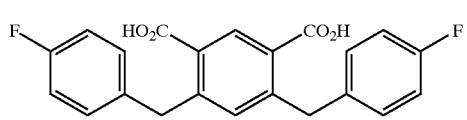
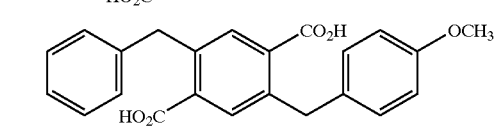
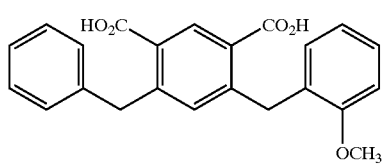
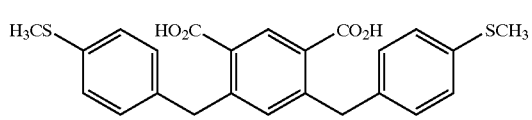
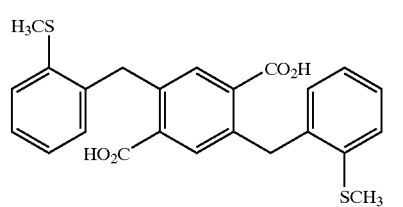
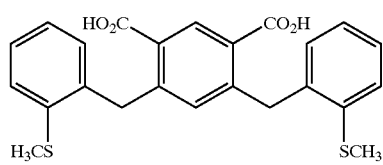

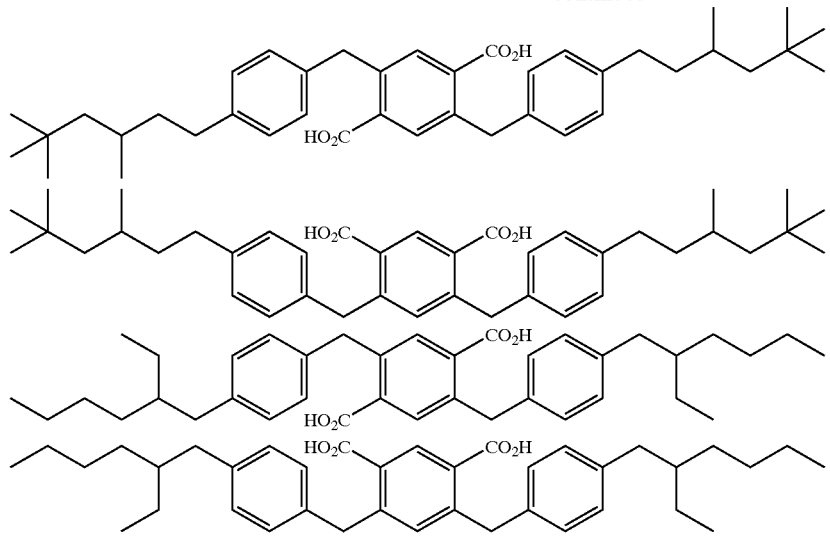

A novel class of the substituted bis(benzyl)phthalic acid compounds can be represented by the following general formulas:

Formula IV(a)

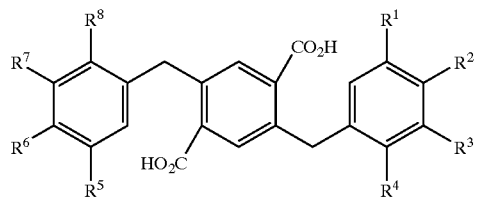

Formula IV(b)

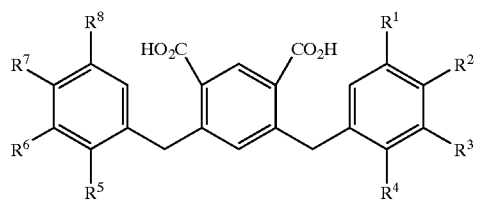

wherein each R (that is, each of the groups $R^1$ through $R^8$) is independently selected from the group consisting of electron-donating groups, halogen atoms, hydrogen atoms, and monovalent combinations thereof. Preferably, each R is independently selected from the group consisting of alkyl groups, alkoxy groups, thioalkoxy groups, halogen atoms, hydrogen atoms, and monovalent combinations thereof. More preferably, each R is independently selected from the group consisting of alkyl groups, alkoxy groups, hydrogen atoms, and monovalent combinations thereof. Even more preferably, each R is independently selected from the group consisting of alkyl groups and hydrogen atoms. Most preferably, each R is independently selected from the group consisting of methyl, n-hexyl, n-nonyl, n-dodecyl, sec-butyl, 3,5,5-trimethylhexyl, 2-ethylhexyl, and hydrogen.

Preferably, only $R^2$ and $R^6$ of the substituted bis(benzyl) terephthalic acids (or $R^2$ and $R^7$ of the substituted bis(benzyl)isophthalic acids) are moieties other than hydrogen. That is, preferably, $R^2$ and $R^6$ of the substituted bis(benzyl) terephthalic acids (or $R^2$ and $R^7$ of the substituted bis(benzyl)isophthalic acids) are independently selected from the group consisting of electron-donating groups, halogen atoms, and monovalent combinations thereof, and $R^1$, $R^3$, $R^4$, $R^5$, $R^7$, and $R^8$ of the substituted bis(benzyl)terephthalic acids (or $R^1$, $R^3$, $R^4$, $R^5$, $R^6$, and $R^8$ of the substituted bis(benzyl)isophthalic acids) are hydrogen.

More preferably, said $R^2$ and $R^6$ (or said $R^2$ and $R^7$) are independently selected from the group consisting of alkyl groups, alkoxy groups, thioalkoxy groups, halogen atoms, and monovalent combinations thereof, and said $R^1$, $R^3$, $R^4$, $R^5$, $R^7$, and $R^8$ (or said $R^1$, $R^3$, $R^4$, $R^5$, $R^6$, and $R^8$) are hydrogen. Still more preferably, said $R^2$ and $R^6$ (or said $R^2$ and $R^7$) are independently selected from the group consisting of alkyl groups, alkoxy groups, and monovalent combinations thereof, and said $R^1$, $R^3$, $R^4$, $R^5$, $R^7$, and $R^8$ (or said $R^1$, $R^3$, $R^4$, $R^5$, $R^6$, and $R^8$) are hydrogen.

Even more preferably, said $R^2$ and $R^6$ (or said $R^2$ and $R^7$) are independently alkyl, and said $R^1$, $R^3$, $R^4$, $R^5$, $R^7$, and $R^8$ (or said $R^1$, $R^3$, $R^4$, $R^5$, $R^6$, and $R^8$) are hydrogen.

Most preferably, said $R^2$ and $R^6$ (or said $R^2$ and $R^7$) are independently selected from the group consisting of methyl, n-hexyl, n-nonyl, n-dodecyl, sec-butyl, 3,5,5-trimethylhexyl, and 2-ethylhexyl, and said $R^1$, $R^3$, $R^4$, $R^5$, $R^7$, and $R^8$ (or said $R^1$, $R^3$, $R^4$, $R^5$, $R^6$ and $R^8$) are hydrogen.

Preparation of Substituted Pentacene Compounds

The cyclization step of the process of the invention can be accomplished via intramolecular Friedel-Crafts cyclization of the substituted bis(benzyl)phthalic acids to form the corresponding substituted pentacenediones (the substituted 7,14-dihydropentacene-5,12-diones and the substituted pentacene-5,7(12H,14H)-diones; hereinafter, the "5,12-diones" and the "5,7-diones"), a novel class of compounds that can be represented by the following general formulas:

Formula V(a)

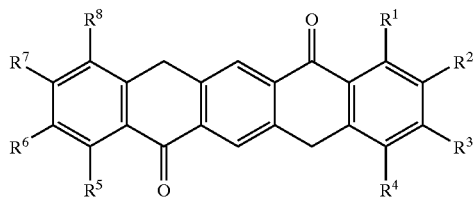

Formula V(b)

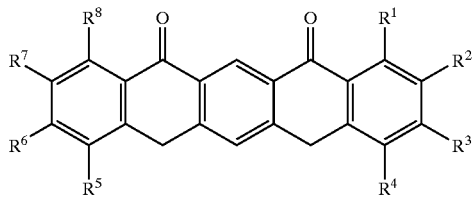

wherein each R (that is, each of the groups $R^1$ through $R^8$) is as defined above for Reaction Scheme A (where the preferences stated for the substituted bis(benzoyl) terephthalic acids correspond to preferences for the 5,12-diones (and the preferences stated for the substituted bis (benzoyl)isophthalic acids correspond to preferences for the 5,7-diones)).

The use of acid catalyzed Friedel-Crafts cyclization to form cyclic ketones is well known in literature and has been described, for example, by Premasagar et al. in J. Org. Chem., 46(14), 2974 (1981); by Allen et al. in Tetrahedron, 33(16), 2083 (1977); and by Hulin et al. in J. Org. Chem., 49, 207 (1984). These reactions can generally be carried out at about 0° C. to 100° C. in the presence of a strong acid such as concentrated sulfuric acid, fuming sulfuric acid, polyphosphoric acid or anhydrous hydrofluoric acid. For example, unsubstituted bis(benzoyl)phthalic acid (2,5-dibenzoylterephthalic acid or 4,6-dibenzoylisophthalic acid) will form the corresponding tetrone when heated to 100° C. with concentrated sulfuric acid for several hours.

However, both the above-described substituted bis (benzyl)phthalic acids and the corresponding substituted bis(benzoyl)phthalic acids are usually unreactive under these conditions. It appears that, in general, the intramolecular Friedel-Crafts cyclization of these substituted compounds cannot be readily accomplished with the strong acids that are typically used for this type of reaction. It has been discovered, however, that Friedel-Crafts cyclization of substituted bis(benzyl)phthalic acids to form the corresponding substituted pentacenediones can be accomplished using an acid composition comprising trifluoromethanesulfonic acid at room temperature or, optionally, at elevated temperatures (for example, a temperature in the range of about 20° C. to 60° C.) and, preferably, with agitation of the reaction mixture.

This cyclization method can be extended to other substituted diaryl carboxylic acids, as well as to unsubstituted diaryl carboxylic acids (for example, 2,5-dibenzyl terephthalic acid and 4,6-dibenzylisophthalic acid which can be cyclized to the corresponding pentacenediones and then reduced and dehydrated to form pentacene). Surprisingly, the method enables the cyclization of such carboxylic acids at lower temperatures than those generally required when using conventional acids such as sulfuric acid. The use of trifluoromethanesulfonic acid also avoids the formation of sulfonated by-products that can occur when sulfuric acid is utilized.

Thus, the method enables the preparation of a broad class of diaryl cyclic ketones by cyclizing a compound comprising at least two aromatic rings, one of the rings having at least one aromatic ring carbon atom that is directly bonded to a carboxylic acid moiety, and the other of the rings having at least one aromatic ring carbon atom that is capable of undergoing aromatic electrophilic substitution with the carboxylic acid moiety using an acid composition comprising trifluoromethanesulfonic acid as shown, for example, below:

Reaction Scheme C

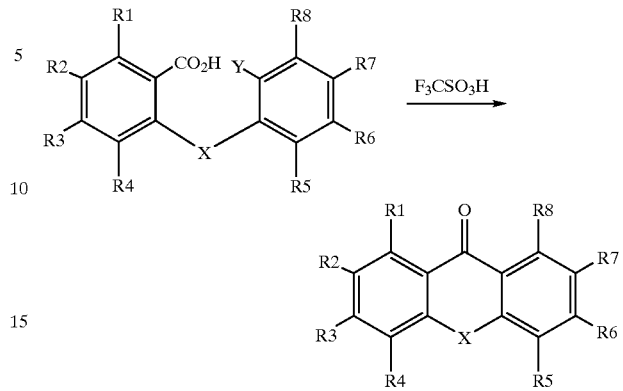

wherein each R (that is, each of the groups $R^1$ through $R^8$) is independently selected from the group consisting of electron-donating groups, electron withdrawing groups (for example, carboxylic acid or a fluoro group), halogen atoms, hydrogen atoms, and combinations thereof; X is a linking group; and Y is a group capable of being a leaving group in a Friedel-Crafts reaction (such as, for example, hydrogen, silyl, substituted silyl, or halogen).

Preferably, X is a covalent bond or a linear or branched alkylene moiety that can optionally contain one or more heteroatoms (for example, nitrogen, oxygen, or sulfur). Preferably, the diaryl carboxylic acid is substituted.

In carrying out the cyclization, trifluoromethanesulfonic acid can be used alone or in combination with, for example, trifluoroacetic acid, or a perfluoroalkanesulfonic acid of higher molecular weight than trifluoromethanesulfonic acid, or a neutral solvent that will not react with trifluoromethanesulfonic acid (for example, a hydrocarbon solvent, a chlorinated solvent such as methylene chloride or a fluorinated solvent) or a Lewis acid (for example, antimony pentafluoride).

Representative examples of this reaction include the following:

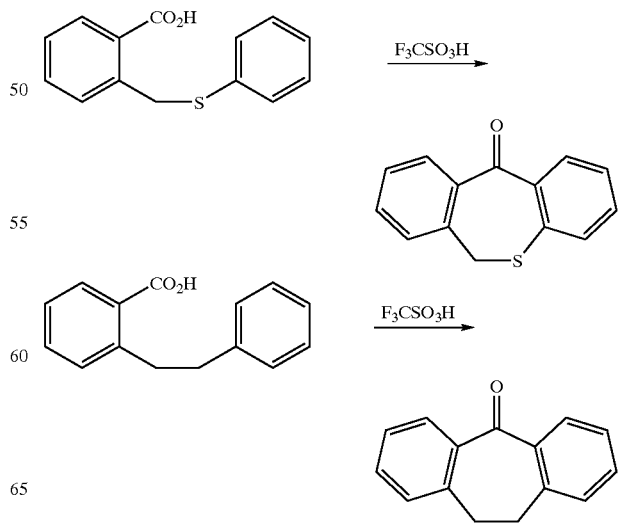

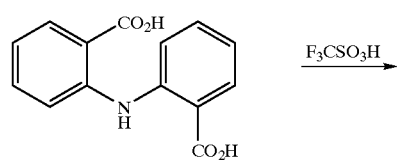
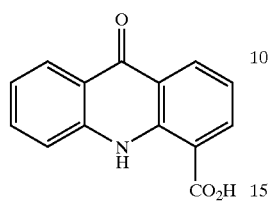
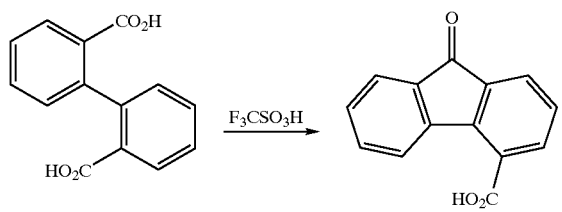
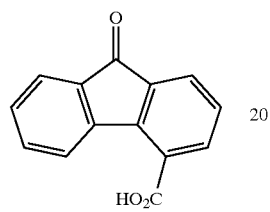
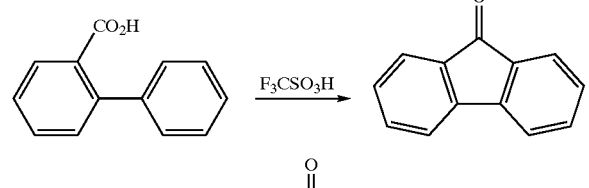
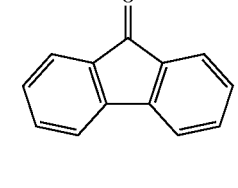
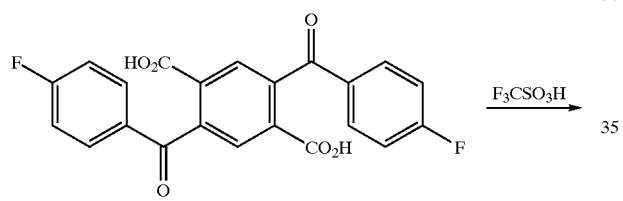
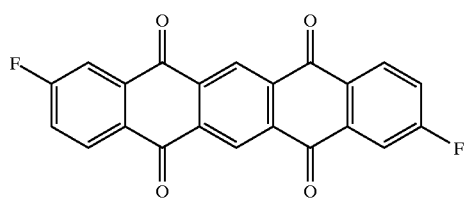
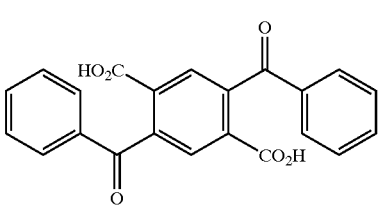
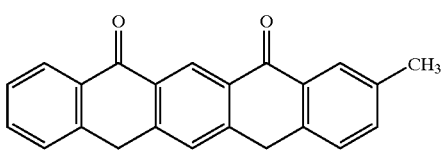
Representative examples of substituted pentacenediones that can be prepared by this process include the following:
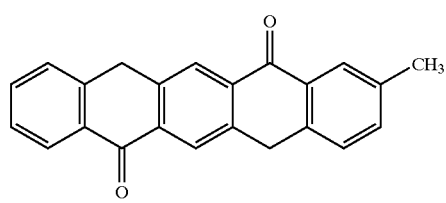
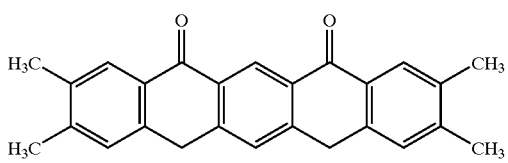
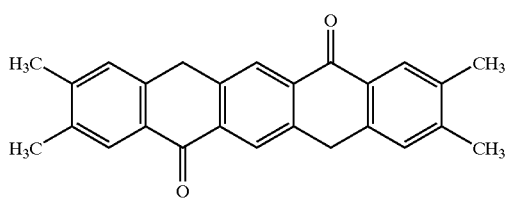
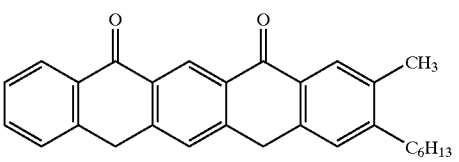
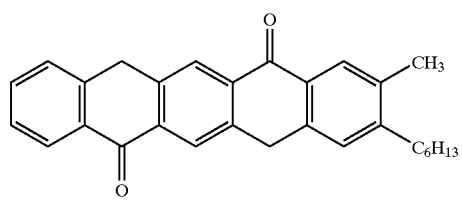

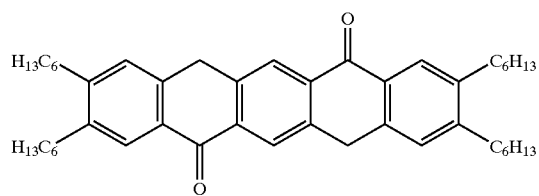
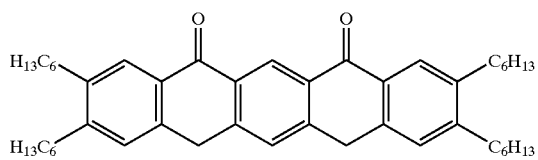
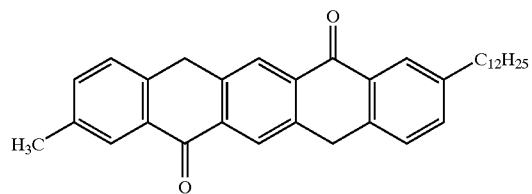
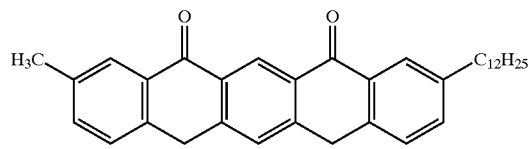
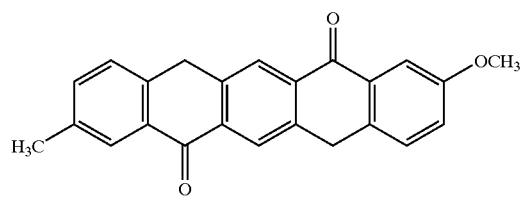
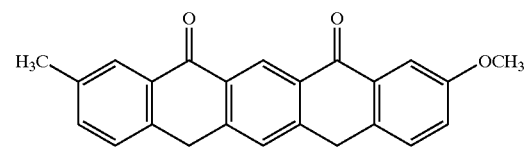
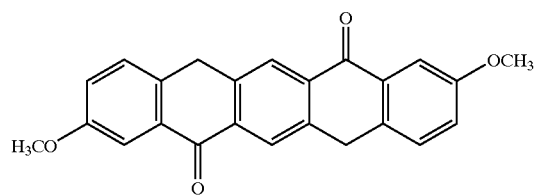
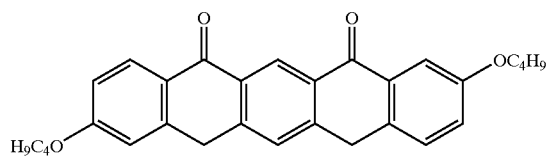
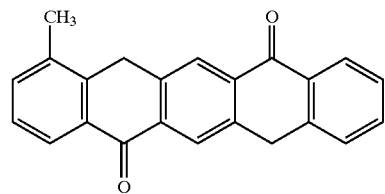
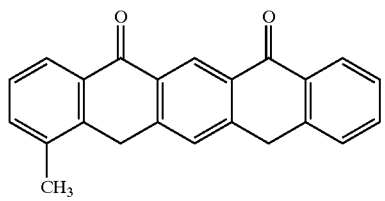
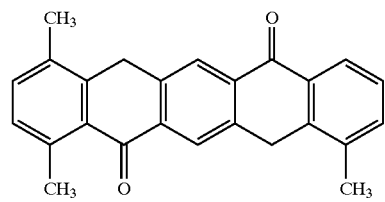
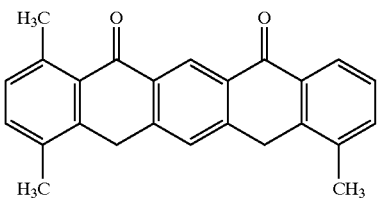
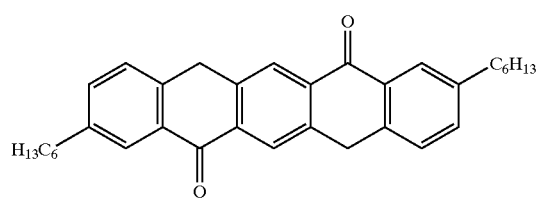
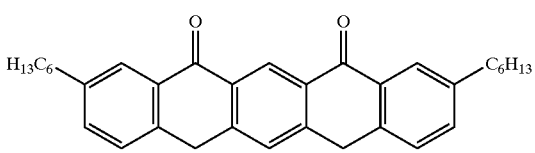
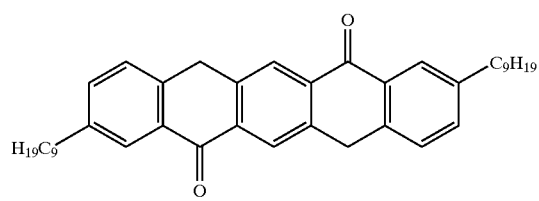
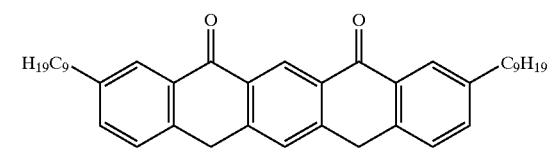

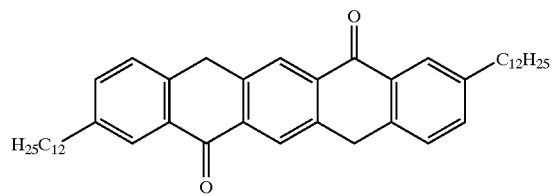
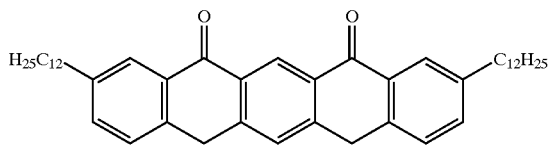
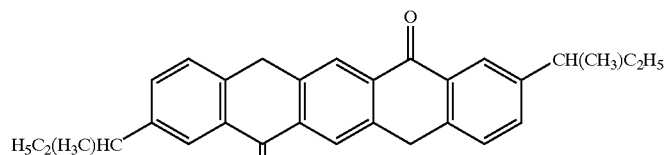
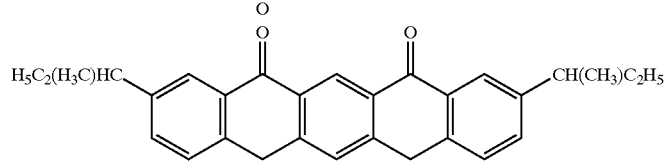
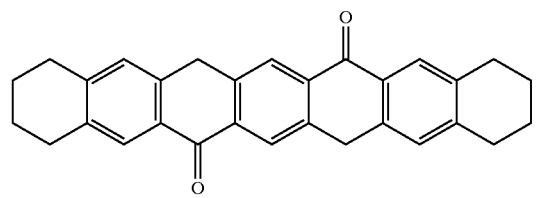
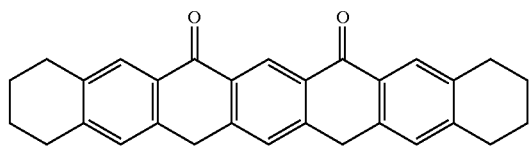
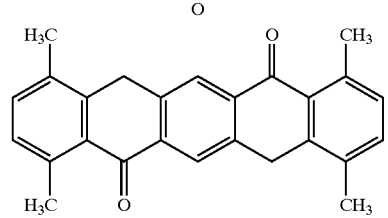
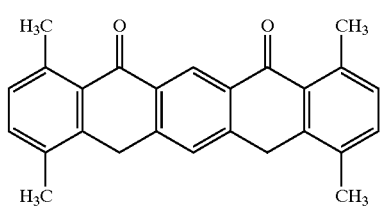
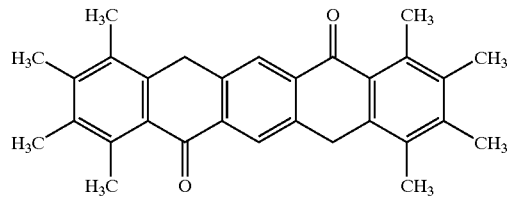
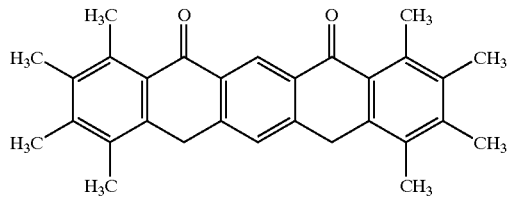
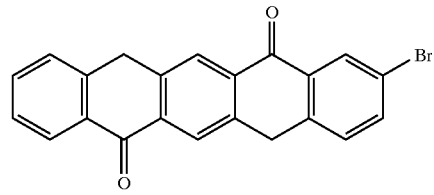
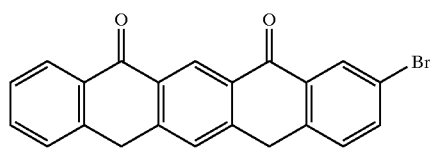
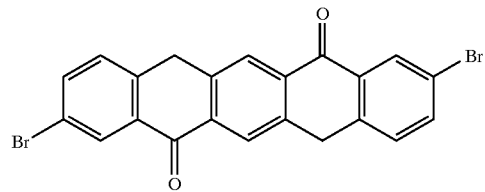
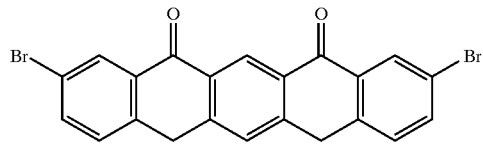
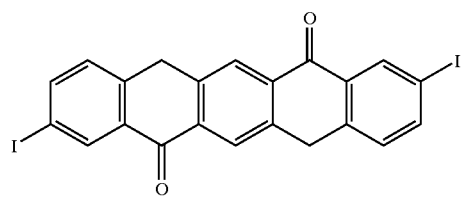
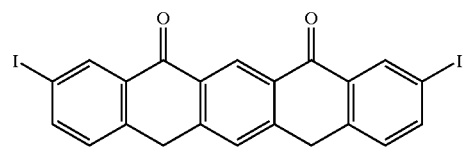

-continued
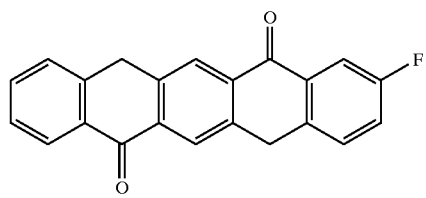
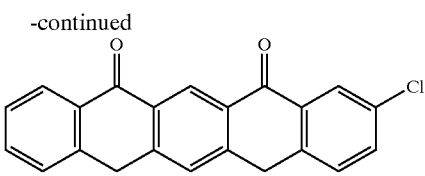
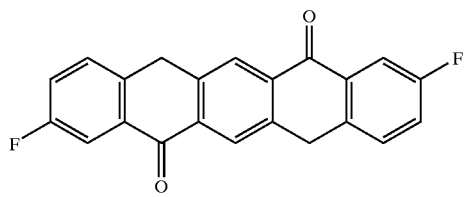
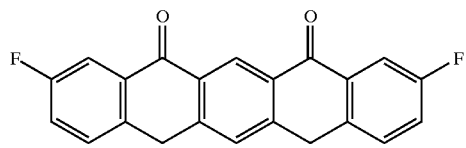
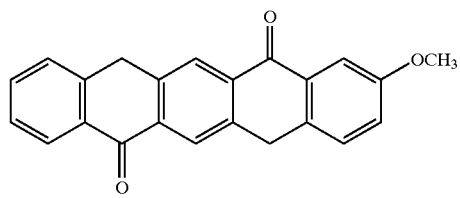
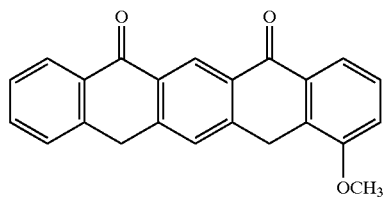
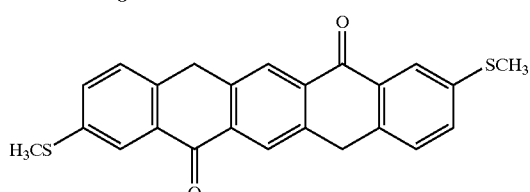
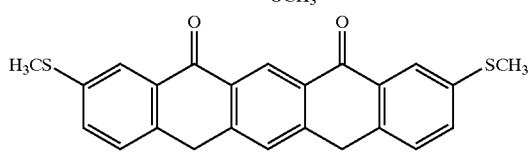
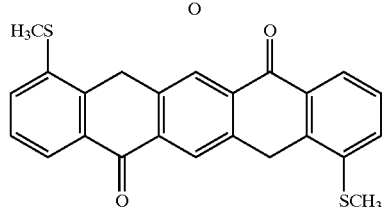
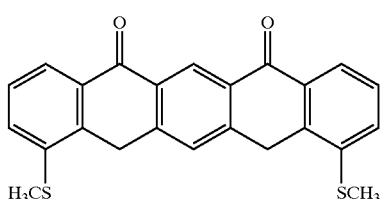
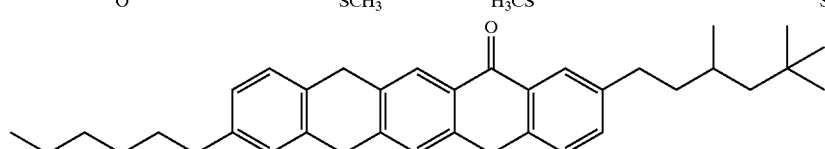
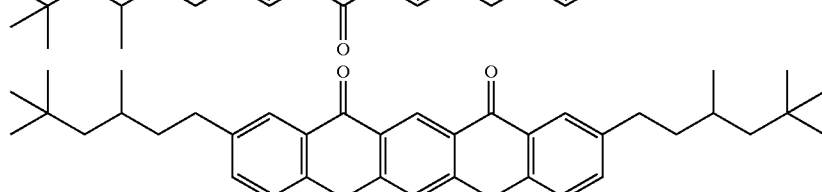
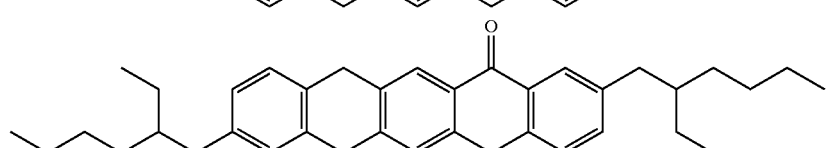
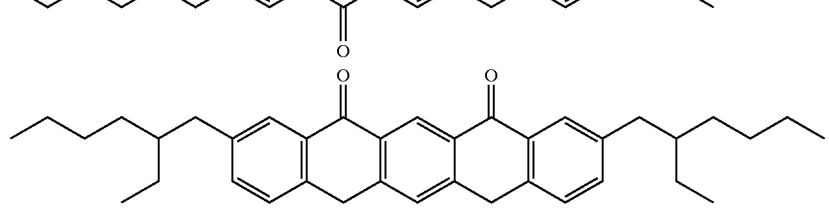

The resulting substituted pentacenediones can be reduced and dehydrated to give the corresponding substituted pentacenes. Good yields can usually be obtained by, for example, a sodium borohydride reduction procedure, as shown, for example, below:

Reaction Scheme D

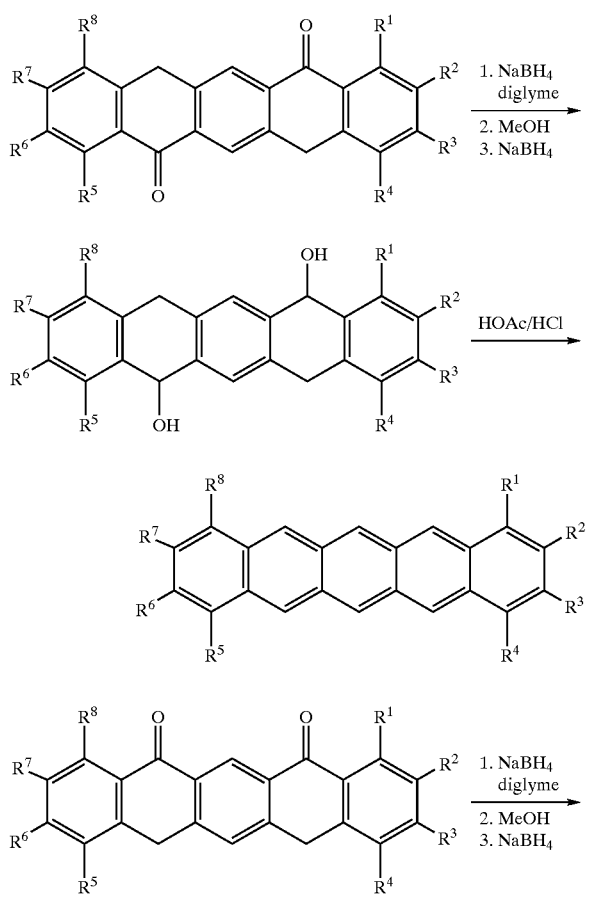

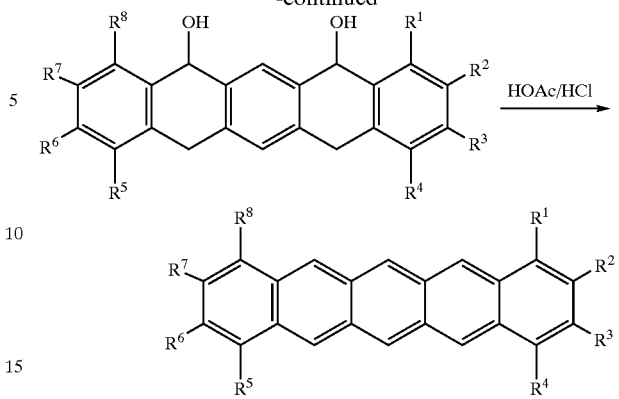

wherein each R (that is, each of the groups $R^1$ through $R^8$) is as defined above for Reaction Scheme A (where the preferences stated above for the substituted bis(benzoyl) phthalic acids correspondingly apply to the substituted pentacenediones, the substituted pentacenediols, and the substituted pentacenes).

Treatment of the diones with sodium borohydride in solvent, such as alcohol(s) or ether(s) (preferably, diglyme) or a combination thereof, preferably followed by addition of methanol and then treatment with additional sodium borohydride gives the corresponding substituted diols. The diols can then be dehydrated to substituted pentacenes by treatment with an acid (for example, hydrochloric acid), preferably with application of heat (for example, heating to about 50° C. to 60° C.) and agitation. Suitable acids include, for example, acetic acid, phosphoric acid, hydrochloric acid, sulfuric acid, hydroiodic acid, hydrobromic acid, trifluoroacetic acid, and trifluoromethanesulfonic acid. Optionally, the diols can be first treated with a weak acid such as acetic acid, followed by treatment with a stronger acid such as hydrochloric acid. Representative examples of substituted pentacenes that can be prepared by this process include:

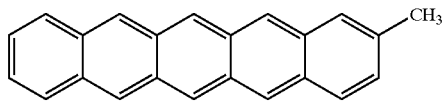

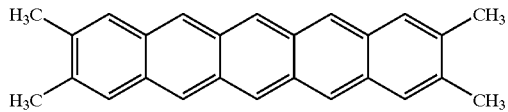

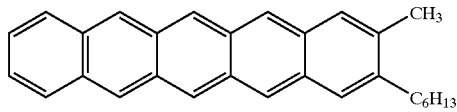

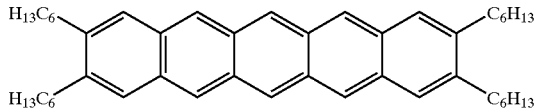

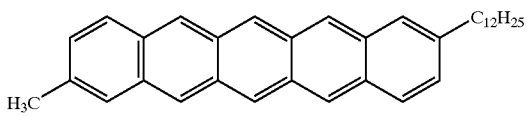

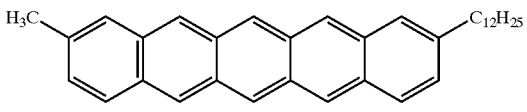

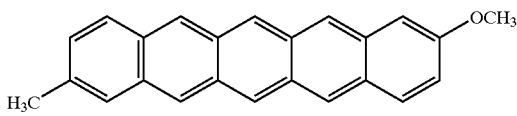

-continued
33
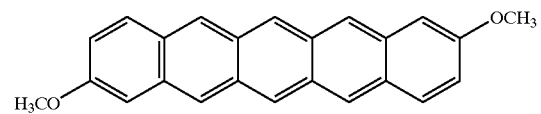
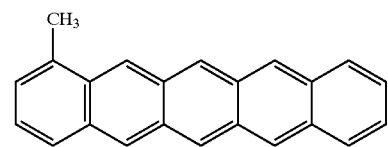
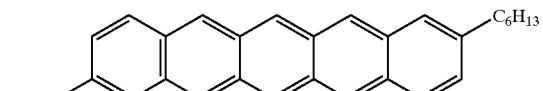
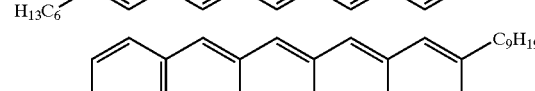
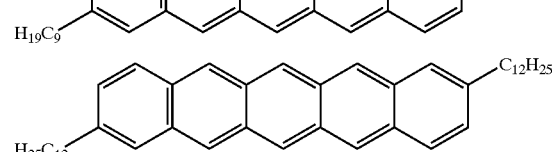
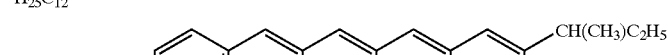
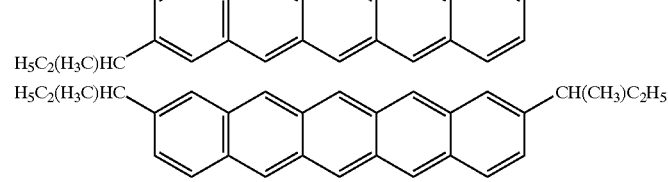
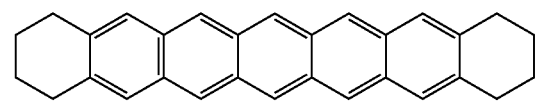
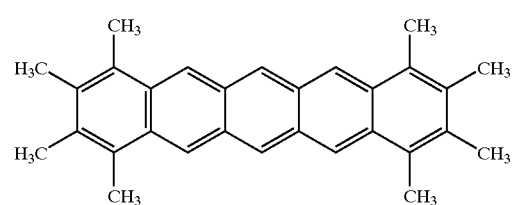
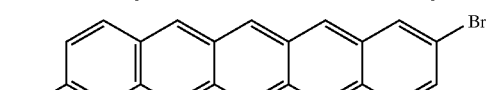
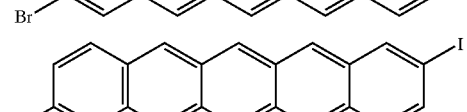
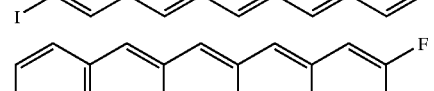
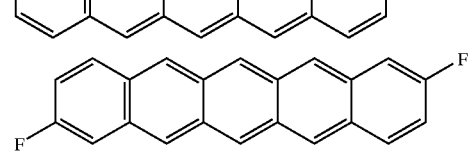
34
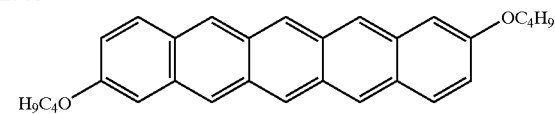
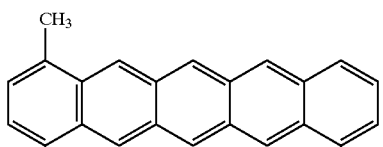
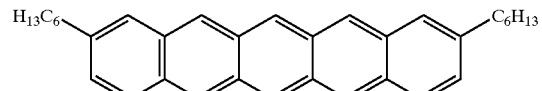
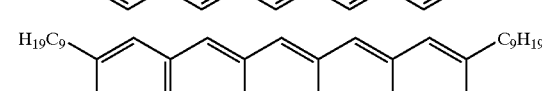
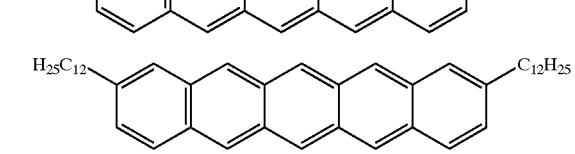
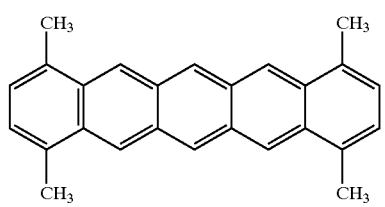
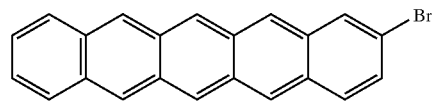
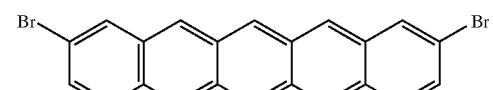
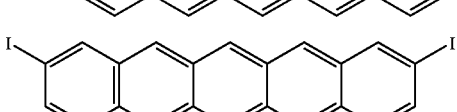
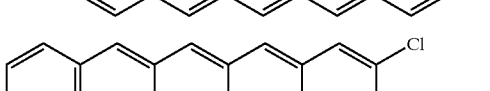
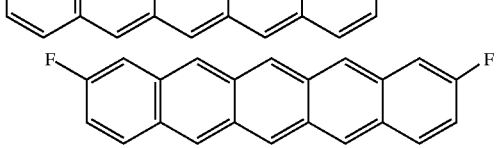

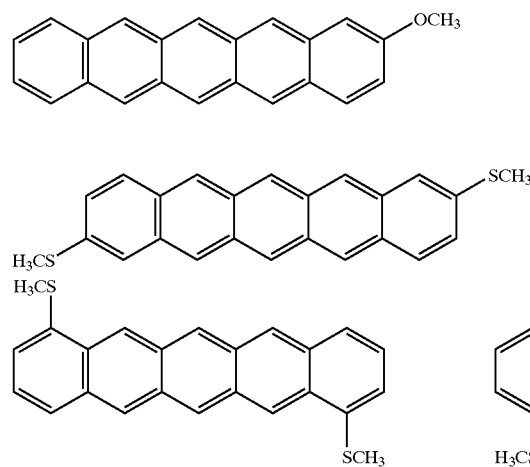
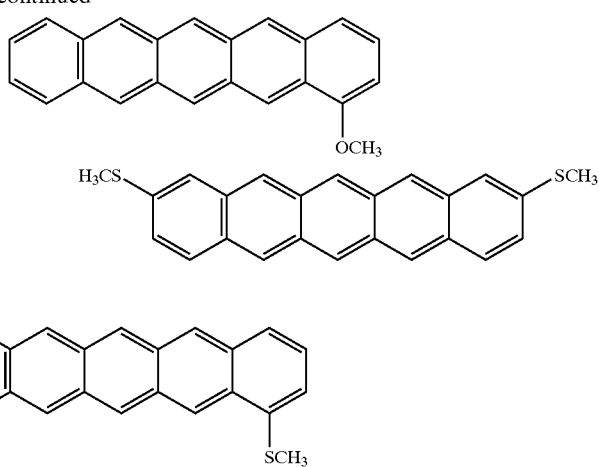
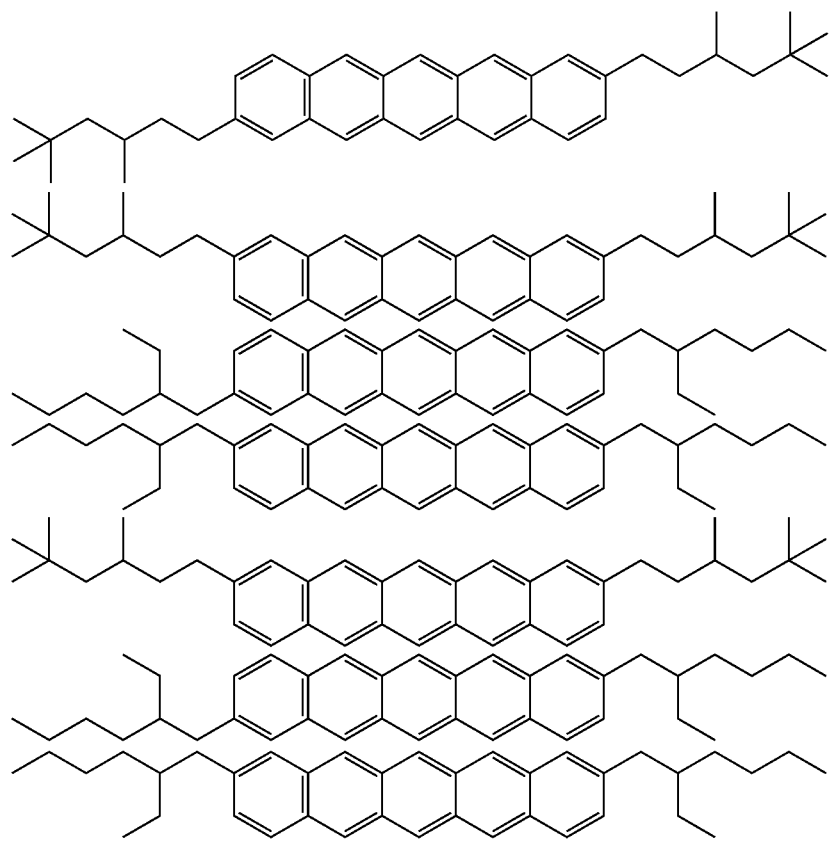

It is possible to over reduce the substituted pentacenediones to substituted dihydropentacenes and then oxidize to obtain the corresponding substituted pentacenes. It has been discovered, however, that treatment of the diones with sodium borohydride in diglyme followed by addition of methanol and then treatment with additional sodium borohydride minimizes over-reduction.

Alternatively, substituted pentacenediones can be reduced using an aluminum alkoxide reduction procedure to give the corresponding substituted pentacenes. Traditionally, tricyclohexoxide has been used. Tricyclohexoxide reactions typically involve dissolving aluminum in cyclohexanol using mercury activation (see, for example, Becker et al., J. Am. Chem. Soc., 113, 1121 (1991)). This type of reaction is typically difficult to control due to the sudden evolution of heat and it requires the handling and disposal of the heavy metal mercury. It has been discovered, however, that it is possible to carry out this reaction using aluminum alkoxides (preferably, aluminum alkoxides derived from secondary alcohols; more preferably, aluminum tri(sec-butoxide)) with application of heat (for example, about 100° C.) and, preferably, with agitation. This reaction can be carried out neat or, preferably, in the presence of a solvent (for example, an alcoholic solvent such as cyclohexanol or a hydrocarbon solvent such as dodecylbenzene).

This method can be extended to other diarene-annellated cyclohexanones, as well. Thus, this method enables the preparation of a broad class of acenes by treating at least one diarene-annellated cyclohexanone, cyclohexa-1,2-dione, or cyclohexa-1,4-dione with aluminum alkoxide. Representative examples of diarene-annellated cyclohexanones, cyclohexa-1,2-diones, and cyclohexa-1,4-diones that can be reduced to their corresponding acenes by this method include the following:

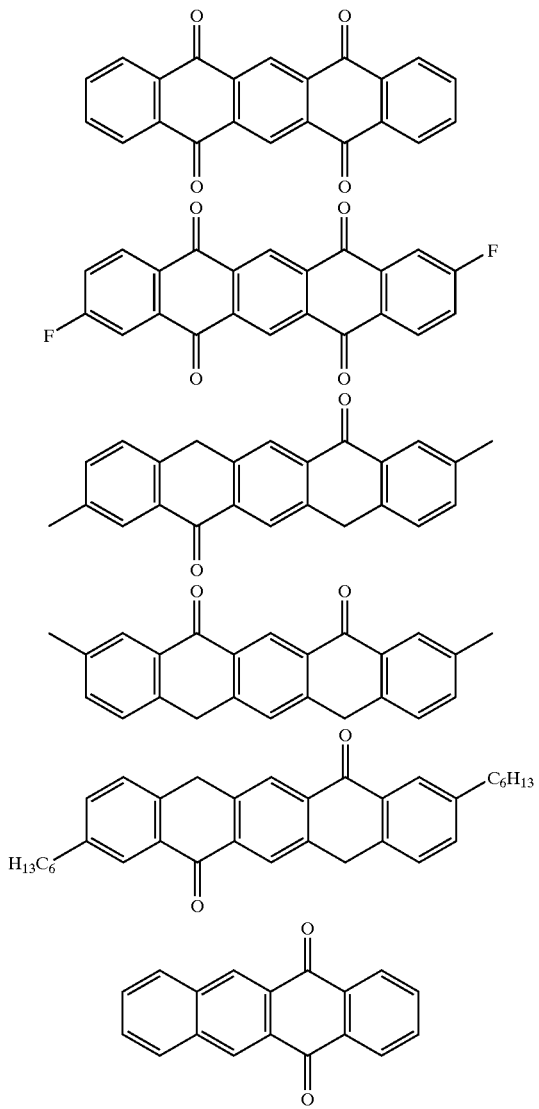

If desired, the resulting substituted pentacenes (or acenes) can be purified by standard methods such as recrystallization, sublimation, or a combination thereof. Purification can be accomplished by sublimation, for example, using a 3-zone furnace (for example, a Thermolyne 79500 tube furnace, available from Barnstead Thermolyne, Dubuque, Iowa) at reduced pressure under a constant flow of nitrogen gas.

The substituted pentacenes prepared by the process of the invention can be used as the semiconductor layer in semiconductor devices, for example, organic thin film transistors.

EXAMPLES

Objects and advantages of this invention are further illustrated by the following examples, but the particular materials and amounts thereof recited in these examples, as well as other conditions and details, should not be construed to unduly limit this invention.

Unless otherwise specified, all starting materials were obtained from Aldrich, Milwaukee, Wis. 2,5-Bis(4-methylbenzoyl)terephthalic and 4,6-bis(4-ethylbenzoyl)isophthalic acids were prepared essentially as described in H. de Diesbach, V. Schmidt, Helv. Chim. Acta, 7, 648 (1924). 2,5-Dibenzoylterephthalic acid and 4,6-dibenzoylisophthalic acid were prepared essentially as described in W. Hobbson, M. Mills, J. Chem. Soc. 101, 2200 (1912).

Example 1

Preparation of 2,9-Dimethylpentacene
Preparation of 2,5-Bis(4-methylbenzyl)terephthalic Acid A mixture of 30.0 grams of 2,5-bis(4-methylbenzoyl)terephthalic acid, 500 mL of acetic acid, and 3 grams of 5% palladium on activated carbon (as a catalyst) was heated to 64° C. for 17 hours in an atmosphere of hydrogen at 270 kPa. The mixture was filtered to remove the catalyst and the product. The catalyst and the product were slurried in 500 mL of tetrahhydrofuran and filtered through Celite™ diatomaceous earth filter agent. The resulting filtrate was concentrated in vacuo. The resulting wet solid was slurried in ethyl acetate and collected by filtration and dried to give 2,5-bis(4-methylbenzyl)terephthalic acid.

Preparation of 7,14-Dihydro-3,10-dimethylpentacene-5,12-dione

To a mixture of 12.7 grams of 2,5-bis(4-methylbenzyl)terephthalic acid and 90 mL of trifluoroacetic acid was added 81.6 grams of trifluoromethanesulfonic acid. The reaction was stirred 22 hours at room temperature. The mixture was poured over 500 grams of ice. The resulting solid precipitate was collected by filtration, washed with 750 mL of saturated aqueous sodium bicarbonate and 1 L of water until the filtrate was neutral to pH paper. The solid was washed with heptane and dried to give 7,14-dihydro-3,10-dimethylpentacene-5,12-dione.

Preparation of 2,9-Dimethylpentacene

A mixture of 24.6 grams of 7,14-dihydro-3,10-dimethylpentacene-5,12-dione in 250 mL of 2-methoxyethyl ether was stirred and flushed with nitrogen for 10 minutes. To this was added in small portions 16.5 grams of sodium borohydride and stirring was continued at room temperature overnight. To the resulting reaction mixture was added slowly over 30 minutes 155 mL of methanol with the temperature maintained below 0° C. The mixture was stirred for 1.5 hours at room temperature. To the mixture was added slowly 360 mL of glacial acetic acid over 10 minutes. The resulting mixture was heated to 60° C. for 1.5 hours. To the mixture was added 100 mL of concentrated hydrochloric acid. The resulting mixture was heated for one hour and cooled to room temperature. To the mixture was added 250 mL of water and stirring was continued for five minutes. The resulting solid was collected by filtration and washed sequentially with 3 L of water, and 1 L of acetone, 1 L of tetrahydrofuran, and 1 L of acetone and dried to give 2,9-dimethylpentacene.

Example 2

Preparation of 2,10-Dimethylpentacene
Preparation of 4,6-Bis(4-methylbenzyl)isophthalic Acid A mixture of 21.1 grams of 4,6-bis(4 ethylbenzoyl)isophthalic acid, 350 mL of acetic acid, and 2.10 grams of 5% palladium on carbon (as a catalyst) was heated to 65° C. for 17 hours in an atmosphere of hydrogen at 270 kPa. The mixture was filtered through Celite™ diatomaceous earth filter agent to remove the catalyst. The resulting filtrate was concentrated in vacuo to give 4,6-bis(4-methylbenzyl)isophthalic acid.

Preparation of 3,9-Dimethylpentacene-5,7(12H,14H)-dione

To 14.1 grams of 4,6-bis(4-methylbenzyl)isophthalic acid was added 75 mL of trifluoroacetic acid followed by 48 grams of trifluoromethanesulfonic acid. After stirring for 3 days at room temperature, the mixture was poured over 200 g of ice, and the resulting solid was collected by filtration. The solid was washed with 400 mL of saturated aqueous sodium bicarbonate solution, followed by 1100 mL of water until the filtrate was neutral to pH paper. The solid was washed with heptane and dried to give 3,9-dimethylpentacene-5,7(12H,14H)-dione.

Preparation of 2,10-Dimethylpentacene

A mixture of 1 gram of 3,9-dimethylpentacene-5,7(12H,14H)-dione and 10 mL of 2-methoxyethyl ether was stirred and flushed with nitrogen for 15 minutes. To this was added 0.948 grams of sodium borohydride and stirring was continued at room temperature overnight. To the mixture was added 6.3 mL of methanol and stirring was continued for 1.5 hours at room temperature. To the mixture was added 15 mL of acetic acid and 10 mL of concentrated hydrochloric acid. The mixture was stirred for one hour at room temperature followed by heating for one hour at 60° C. To the mixture was added 50 mL of water and the resulting solid was isolated by filtration and washed with water. The solid was washed with tetrahydrofuran until a pale filtrate resulted. The solid was washed with heptane and dried under an atmosphere of nitrogen to give 2,10-dimethylpentacene.

Example 3

Preparation of 2,9-Dihexylpentacene

Preparation of 2,5-Bis(4-hexylbenzoyl)terephthalic Acid

To a mixture of 25.7 grams of aluminum chloride, 51.3 mL of 1,2-dichloroethane, and 10 grams of benzene-1,2,4,5-tetracarboxylic acid dianhydride (pyromellitic dianhydride) was added with cooling, a solution of 14.9 grams of hexylbenzene and 6.40 grams of diisopropylethylamine in 25 mL of 1,2-dichloroethane over a period of 3.5 hours, keeping the temperature between 15° C. and 20° C. The resulting mixture was stirred for an additional 15 minutes after the addition was complete, and it was then heated to 40° C. for one hour. The warm mixture was poured into a beaker with 200 grams of ice and 75 mL of concentrated hydrochloric acid and stirred overnight at room temperature. The aqueous phase was poured off, and the resulting oily solid was stirred with 500 mL of water, and the water was poured off. This water wash was repeated, and the resulting residue was dissolved in 250 mL of acetone and concentrated in vacuo. This residue was stirred with 55 mL of ethyl acetate, and the resulting solid was collected by filtration, washed with 100 mL of ethyl acetate, and dried to give 2,5-bis(4-hexylbenzoyl)terephthalic acid.

Preparation of 2,5-Bis(4-hexylbenzyl)terephthalic Acid

A mixture of 5.26 grams of 2,5-bis(4-hexylbenzoyl)terephthalic acid, 100 mL of tetrahydrofuran, and 0.53 grams of 5% palladium on carbon (as a catalyst) was heated at 65° C. for 17 hours in an atmosphere of hydrogen at 270 kPa. The resulting mixture was filtered through Celite™ diatomaceous earth filter agent to remove the catalyst. The filtrate was concentrated in vacuo to give 2,5-bis(4-hexylbenzyl)terephthalic acid.

Preparation of 3,10-Dihexyl-7,14-dihydropentacene-5,12-dione

A mixture of 2.56 grams of 2,5-bis(4-hexylbenzyl)terephthalic acid, 25.6 grams of trifluoroacetic acid, and 12.8 gram of trifluoromethanesulfonic acid was stirred overnight at room temperature. The resulting mixture was poured over 200 grams of ice. The solid was collected by filtration and washed with saturated aqueous sodium bicarbonate solution and then with 400 mL of water until the filtrate was neutral to pH paper. The solid was dried to give 3,10-dihexyl-7,14-dihydropentacene-5,12-dione.

Preparation of 2,9-Dihexylpentacene

A mixture of 20 grams of 3,10-dihexyl-7,14-dihydropentacene-5,12-dione and 200 mL of 2-methoxyethyl ether was stirred and flushed with nitrogen for 15 minutes. To this was added 13.4 grams of sodium borohydride, and stirring was continued at room temperature overnight. To the resulting mixture was added 126 mL of methanol over 1.25 hours. The temperature increased to 40° C. and was maintained at 40° C. during the addition by intermittent application of a cold water bath. When addition was complete stirring was continued at room temperature. After stirring for 2 hours at room temperature an additional 50 mL of 2-methoxyethyl ether was added. After stirring with methanol for a total of 3.5 hours, 300 mL of acetic acid was added, and the resulting mixture was heated to 60° C. for 1.5 hours. To the mixture was added 100 mL of concentrated hydrochloric acid and heating at 60° C. was continued for one hour. The mixture was cooled to room temperature and the resulting solid was collected by filtration and washed with 500 mL of water. The solid was washed with 500 mL of acetone and then 60 mL of tetrahydrofuran. The solid was washed with an additional one liter of acetone and dried to give 2,9-dihexylpentacene.

Example 4

Preparation of 2,9-Dinonylpentacene

Preparation of 2,5-Bis(4-nonylbenzoyl)terephthalic Acid

To a mixture of 1370 grams of aluminum chloride, 533.7 grams of benzene-1,2,4,5-tetracarboxylic acid dianhydride and 2750 mL of 1,2-dichloroethane stirred at 15° C. was added a solution of 341.5 grams of N,N-diisopropylethylamine in 1334 mL of 1,2-dichloroethane over a period of 3.5 hr, keeping the reaction temperature between 15° C. and 20° C. The resulting reaction mixture was stirred overnight at room temperature. The reaction mixture was added to a mixture of 2500 grams of ice and 2500 mL of concentrated hydrochloric acid with efficient stirring. The mixture was divided into 800 mL portions and each portion was worked up as follows. To 800 mL of the mixture was added 800 mL of tetrahydrofuran, 800 mL of ethyl acetate and 800 mL of water. The mixture was stirred and phase split. The organic phase was filtered and the filtrate was concentrated in vacuo. The resulting residues were combined. To 711 grams of the combined residue was added 4 L of acetone and the mixture was stirred until a suspension of a fine solid resulted. The solid was collected by filtration and washed with 1 L of acetone. The solid was dried to give 2,5-bis(4-nonylbenzoyl)terephthalic acid.

Preparation of 2,5-Bis(4-nonylbenzyl)terephthalic Acid

A mixture of 109 grams of 2,5-bis(4-nonylbenzoyl)terephthalic acid, 1500 mL of tetrahydrofuran, and 7.43 grams of 10% palladium on carbon (as a catalyst) was heated at 65° C. for 17 hours in an atmosphere of hydrogen at 270 kPa. The reaction mixture was filtered through Celite™ diatomaceous earth filter agent to remove the catalyst. The filtrate was concentrated in vacuo to give 2,5-bis(4-nonylbenzyl)terephthalic acid.

Preparation of 7,14-Dihydro-3,10-dinonylpentacene-5,12-dione

A mixture of 26.3 grams of 2,5-bis(4-nonylbenzyl)terephthalic acid and 100 mL of trifluoromethanesulfonic acid was heated to 60° C. and maintained for one hour. The mixture was cooled to room temperature and poured over 500 grams of ice. The resulting solid was collected by filtration and washed sequentially with one liter of water, two liters of saturated aqueous sodium bicarbonate solution, and four liters of water until the filtrate was neutral to pH paper. The solid was washed with two liters of acetone and dried to give 7,14-dihydro-3,10-dinonylpentacene-5,12-dione.

Preparation of 2,9-Dinonylpentacene

A mixture of 20 grams of 7,14-dihydro-3,10-dinonylpentacene-5,12-dione and 400 mL of 2-methoxyethyl ether was stirred and flushed with nitrogen for 15 minutes. To this was added 11.4 grams of sodium borohydride and stirring was continued at 60° C. for 18 hours. The resulting mixture was cooled to room temperature, 3.0 grams of sodium borohydride was added, and stirring was continued for 16 hours at room temperature. To the resulting mixture was added 170 mL of acetic acid, and the mixture was heated at 60° C. for one hour. To this mixture was added 120 mL of concentrated hydrochloric acid and heating was continued at 60° C. for one hour. The resulting mixture was cooled to room temperature and the resulting solid was collected by filtration and dried to give 2,9-dinonylpentacene.

Example 5

Preparation of 2,9-Didodecylpentacene

Preparation of 2,5-Bis(4-dodecylbenzoyl)terephthalic Acid

To a mixture of 492 grams of aluminum chloride and 988 mL of 1,2-dichloroethane was added 192 grams of benzene-1,2,4,5-tetracarboxylic acid dianhydride (pyromellitic dianhydride). The resulting mixture was cooled to 16° C. and a solution of 434 grams of 1-dodecylbenzene, 123 grams of diisopropylethylamine and 480 mL of 1,2-dichloroethane was added over a period of 3.5 hours, keeping the temperature between 15° C. and 20° C. during the addition. The mixture was stirred overnight at room temperature and poured into a beaker of 1000 grams of ice and 1000 grams concentrated hydrochloric acid. The mixture was stirred for one hour and the liquid was poured from the coagulate. The mixture was divided into 800 mL portions and each portion was worked up as follows. To 800 mL of the mixture was added 800 mL of tetrahydrofuran, 800 mL of ethyl acetate and 800 mL of water. The mixture was stirred and phase split. The organic phase was filtered and the filtrate was concentrated in vacuo. The resulting residues were combined. To 127 grams of the combined residue was added 800 mL of ethyl acetate and the resulting mixture was stirred until a suspension of a fine solid resulted. The solid was collected by filtration and washed with 50 mL of ethyl acetate. The solid was dried to give 2,5-bis(4-dodecylbenzoyl)terephthalic acid.

Preparation of 2,5-Bis(4-dodecylbenzyl)terephthalic Acid

A solution of 133 grams of 2,5-bis(4-dodecylbenzoyl)terephthalic acid and 1 L of tetrahydrofuran was treated with 8 grams of 10% palladium on carbon (as a catalyst) and heated to 65° C. for 17 hours in an atmosphere of hydrogen at 270 kPa. The mixture was filtered through Celite™ diatomaceous earth filter agent to remove the catalyst. The filtrate was concentrated in vacuo to give a solid. The solid was triturated with ethyl acetate, and the residue was dried to give 2,5-bis(4-dodecylbenzyl)terephthalic acid.

Preparation of 3,10-Didodecyl-7,14-dihydropentacene-5,12-dione

A mixture of 22.7 grams of 2,5-bis(4-dodecylbenzyl)terephthalic acid and 80 mL of trifluoromethanesulfonic acid was heated to 60° C. for one hour. The mixture was cooled to room temperature and poured over 500 grams of ice. The resulting precipitate was collected by filtration and washed sequentially with one liter of water, two liters of saturated aqueous sodium bicarbonate solution, and four liters of water until the filtrate was neutral to pH paper. The resulting solid was washed with two liters of acetone and dried to give 3,10-didodecyl-7,14-dihydropentacene-5,12-dione.

Preparation of 2,9-Didodecylpentacene

A mixture of 8.5 grams of 3,10-didodecyl-7,14-dihydropentacene-5,12-dione and 250 mL of 2-methoxyethyl ether was stirred and flushed with nitrogen for 15 minutes. To this was added 4.46 grams of sodium borohydride. The resulting mixture was heated to 60° C. for 18 hours. The mixture was cooled to room temperature, and 42 mL of methanol was added slowly. The resulting mixture was stirred at room temperature for 30 minutes. To this was added 1.2 grams of sodium borohydride, and stirring was continued at room temperature for 16 hours. To the resulting mixture was added 60 mL of acetic acid, and the mixture was heated at 60° C. for one hour. To this mixture was added 43 mL of concentrated hydrochloric acid, and heating was continued at 60° C. for one hour. To the resulting mixture was added 100 mL of water and the mixture cooled to room temperature and the solid was collected by filtration and dried to give 2,9-didodecylpentacene.

Example 6

Preparation of 1,2,3,4,10,11,12,13-Octahydroheptacene

Preparation of 2,5-Bis(5,6,7,8-tetrahydronaphthalene-2-carbonyl)terephthalic Acid and 4,6-Bis(5,6,7,8-tetrahydronaphthalene-2-carbonyl)isophthalic Acid A mixture of 250 grams of aluminum chloride, 500 mL of 1,2-dichloroethane, and 97.4 grams of benzene-1,2,4,5-tetracarboxylic acid dianhydride (pyromellitic dianhydride) was cooled to 15° C., and a solution of 124.1 grams of 1,2,3,4-tetrahydronaphthalene, 48.79 grams of triethylamine, and 243 mL of 1,2-dichloroethane was added slowly dropwise over a period of 1.5 hours keeping the temperature between 15-20° C., followed by stirring overnight at room temperature. The resulting mixture was poured into 1600 grams of ice and 400 grams of concentrated hydrochloric acid and stirred for 20 minutes at room temperature. The top aqueous layer was poured off, and the remaining mixture was diluted with 2 L of ethyl acetate and stirred until a homogeneous solution resulted. The resulting mixture was phase split, and the organic phase was filtered. The organic phase was washed with 600 mL of brine, dried over magnesium sulfate, filtered, and concentrated in vacuo. To the resulting residue was added 500 mL of isopropyl acetate, and the resulting mixture was stirred at room temperature. The residue was treated with additional isopropyl acetate and heptane to crystallize the product. The resulting solid product was isolated, washed with heptane, and dried to give a mixture of 2,5-bis(5,6,7,8-tetrahydronaphthalene-2-carbonyl)terephthalic acid and 4,6-bis(5,6,7,8-tetrahydronaphthalene-2-carbonyl)isophthalic acid.

Preparation of 2,5-Bis(5,6,7,8-tetrahydronaphthalen-2-ylmethyl)terephthalic Acid and 4,6-Bis(5,6,7,8-tetrahydronaphthalen-2-ylmethyl)isophthalic Acid A mixture of 94.7 grams of 2,5-bis(5,6,7,8-tetrahydronaphthalene-2-carbonyl)terephthalic acid and 4,6-bis(5,6,7,8-tetrahydronaphthalene-2-carbonyl)isophthalic acid, 1 L of tetrahydrofuran, and 6 grams of 10% palladium on carbon (as a catalyst) was heated at 65° C. for 17 hours in an atmosphere of hydrogen at 270 kPa. The reaction mixture was filtered through Celite™ diatomaceous earth filter agent to remove the catalyst. The filtrate was concentrated in vacuo to give a solid. The solid was triturated with ethyl acetate, collected by filtration, and dried to give a mixture of 2,5-bis(5,6,7,8-tetrahydronaphthalen-2-ylmethyl)terephthalic acid and 4,6-bis(5,6,7,8-tetrahydronaphthalen-2-ylmethyl)isophthalic acid.

Preparation of 1,2,3,4,8,10,11,12,13,17-Decahydroheptacen-6,15-dione and 1,2,3,4,10,11,12,13-Octahydroheptacen-6,8(15H,17H)-dione To a mixture of 35.3 grams of 2,5-bis(5,6,7,8-tetrahydronaphthalen-2-ylmethyl)terephthalic acid and 4,6-bis(5,6,7,8-tetrahydronaphthalen-2-ylmethyl)isophthalic acid was added 120 grams of trifluoromethanesulfonic acid. The mixture was stirred at room temperature for one hour followed by heating to 60° C. for six hours. The mixture was poured over 500 grams of ice. The resulting solid was isolated by filtration and washed sequentially with 500 mL of saturated aqueous sodium bicarbonate solution and 4 L of water until the filtrate was neutral to pH paper. The solid was dried to give a mixture of 1,2,3,4,8,10,11,12,13,17-decahydroheptacen-6,15-dione and 1,2,3,4,10,11,12,13-octahydroheptacen-6,8(15H,17H)-dione.

Preparation of 1,2,3,4,10,11,12,13-Octahydroheptacene

A mixture of 1.0 gram of 1,2,3,4,8,10,11,12,13,17-decahydroheptacen-6,15-dione and 1,2,3,4,10,11,12,13-octahydroheptacen-6,8(15H,17H)-dione and 20 mL of 2-methoxyethyl ether was stirred and flushed with nitrogen for 15 minutes. To this was added 0.766 grams of sodium borohydride. The resulting mixture was stirred overnight at room temperature. To the mixture was added 7.2 mL of methanol and stirring was continued for 30 minutes. To the resulting mixture was added 0.2 grams of sodium borohydride, and stirring was continued at room temperature for 5 hours. The resulting mixture was heated to 60° C. for one hour. To the mixture was added 11.4 mL of glacial acetic acid and 7.3 mL of concentrated hydrochloric acid. The resulting mixture was heated at 60° C. for one hour. To this mixture was added 20 mL of water and the resulting solid was collected by filtration. The solid was washed with water followed by acetone followed by tetrahydrofuran and dried to give 1,2,3,4,10,11,12,13-octahydroheptacene.

Example 7

Preparation of 2,9-Di-sec-butylpentacene

Preparation of 2,5-Bis(4-sec-butylbenzoyl)terephthalic Acid

A mixture of 417 grams of aluminum chloride, 837 mL of 1,2-dichloroethane, and 162 grams of benzene-1,2,4,5-tetracarboxylic acid dianhydride (pyromellitic dianhydride) was stirred and cooled to 16° C. To the mixture was added a solution of 200 grams of sec-butylbenzene, 104 grams of diisopropylethylamine and 140 mL of 1,2-dichloroethane over a 3.5 hour period maintaining the reaction temperature between 15° C. and 20° C. The resulting mixture was stirred overnight at room temperature and added slowly to 500 grams of ice and 500 mL of concentrated hydrochloric acid. The mixture was stirred for one hour and the liquid poured from the coagulate. The coagulate was worked up in 500 mL portions as follows. To 500 mL of the coagulate was added 500 mL of water, 500 mL of ethyl acetate and 500 mL of tetrahydrofuran. The mixture was stirred until the solid dissolved and then phase split. The organic phase was filtered and concentrated in vacuo. To 178 grams of the residue was added 178 mL of ethyl acetate and 1600 mL of heptane and the mixture was stirred until a suspension of a fine solid formed. The solid was collected by filtration and washed with a mixture of 60 mL of ethyl acetate and 540 mL of heptane. The solid was treated with 982 mL of ethyl acetate and 392 mL of heptane and stirred. The solid was collected by filtration and washed with a mixture of 120 mL of ethyl acetate and 480 mL of heptane. The solid was dried to give 2,5-bis(4-sec-butylbenzoyl)terephthalic acid Preparation of 2,5-bis(4-sec-butylbenzyl)terephthalic Acid A mixture of 120 grams of 2,5-bis(4-sec-butylbenzoyl) terephthalic acid, 1.5 L of tetrahydrofuran, and 9.65 grams of 10% palladium on carbon (as a catalyst) was heated at 65° C. for 17 hours in an atmosphere of hydrogen at 270 kPa. The reaction mixture was filtered through Celite™ diatomaceous earth filter agent to remove the catalyst. The filtrate was concentrated in vacuo to give a solid. The solid was triturated with 10% ethyl acetate in heptane, collected and dried to give 2,5-bis(4-sec-butylbenzyl)terephthalic acid.

Preparation of 3,10-Di-sec-butyl-7,14-dihydropentacene-5,12-dione

To five mL of trifluoromethanesulfonic acid was added two grams of 2,5-bis(4-sec-butylbenzyl)terephthalic acid. The temperature was maintained between 16° C. and 25° C. during the addition. The mixture was stirred for five days at room temperature. The mixture was poured over ice and the solid was collected by filtration, washed with saturated aqueous sodium bicarbonate and water until the pH of the filtrate was neutral to pH paper. The solid was dried to give 3,10-di-sec-butyl-7,14-dihydropentacene-5,12-dione.

Preparation of 2,9-Di-sec-butylpentacene

A mixture of 2 grams of 3,10-di-sec-butyl-7,14-dihydropentacene-5,12-dione and 45.3 mL of 2-methoxyethyl ether was stirred and flushed with nitrogen for 15 minutes. To this was added 1.52 grams of sodium borohydride and the mixture was heated to 60° C. overnight. The mixture was cooled to room temperature. To the mixture was added 0.4 grams of sodium borohydride and stirring was continued for 30 minutes. To the mixture was added 15 mL of isopropyl alcohol and stirring was continued at room temperature for 5 hours. To the mixture was added 15 mL of methanol. To the mixture was added one gram of sodium borohydride and stirring was continued at room temperature. To the mixture was added 16 mL of acetic acid and the mixture was heated to 60° C. for one hour. To the mixture was added 16 mL of concentrated hydrochloric acid and heating was continued at 60° C. The solid was collected by filtration and washed with water followed by ethyl acetate and then acetone. The solid was dried to give 2,9-di-sec-butylpentacene.

Example 8

Preparation of 1,4,8,11-Tetramethylpentacene

Preparation of 2,5-Bis(2,5-dimethybenzoyl)terephthalic Acid

A mixture of 144 grams of benzene-1,2,4,5-tetracarboxylic acid dianhydride (pyromellitic dianhydride), 439 grams of aluminum chloride, and 915 grams of 1,2-dichloroethane was cooled to 15° C. To this was added a mixture of 140 grams of p-xylene, 109 grams of N,N-diisopropylethylamine, and 426 mL of 1,2-dichloroethane over a period of 3.5 hours keeping the temperature between 15° C. and 20° C. The resulting mixture was stirred overnight at room temperature, poured into 2876 grams of ice and 1078 mL concentrated hydrochloric acid and stirred for one hour. The organic layer was washed with 7 L of water. Three liters of water was poured off and the mixture allowed to stand for 4 days, after which the remaining 3 L of water was poured off. To the resulting residue was added 7 L of ethyl acetate and 3 L of tetrahydrofuran. The organic phase was separated and concentrated in vacuo. To 92 grams of the residue was added 1910 mL of ethyl acetate and the mixture was heated to 77° C. for one hour. The mixture was cooled to room temperature and the solid was collected by filtration and dried to give 2,5-bis(2,5-dimethybenzoyl)terephthalic acid.

Preparation of 2,5-Bis(2,5-dimethybenzyl)terephthalic Acid

A mixture of 92 grams of 2,5-bis(2,5-dimethybenzoyl)terephthalic acid in 1.5 L of tetrahydrofuran was treated with 9.2 grams of 10% palladium on carbon (as a catalyst) in an atmosphere of hydrogen at 270 kPa and 65° C. for 17 hours. The reaction mixture was filtered through Celite™ diatomaceous earth filter agent to remove the catalyst. The filtrate was concentrated in vacuo to give a solid. The solid was triturated with ethyl acetate, collected by filtration, and dried. To 75 grams of the solid was added 1250 grams of acetic acid, and the resulting mixture was heated to 117° C. for 30 minutes and cooled to room temperature. The resulting solid was collected by filtration and washed with acetic acid followed by heptane. The resulting residue was dried to give 2,5-bis(2,5-dimethybenzyl)terephthalic acid.

Preparation of 7,14-Dihydro-1,4,8,11-tetramethylpentacene-5,12-dione

To 200 mL of trifluoromethanesulfonic acid cooled to 18° C. was added slowly 53 grams of 2,5-bis(2,5-dimethylbenzyl)terephthalic acid in small portions as a solid at a rate such that the temperature remained below 25° C. The mixture was allowed to stir for 10 minutes and the cooling bath was removed. The mixture was stirred overnight at room temperature. The mixture was poured over 600 grams of ice and the resulting solid was collected by filtration. The solid was washed with 1 L of water followed by 500 mL of saturated aqueous sodium bicarbonate solution. The solid was washed with water until the pH of the filtrate was neutral to pH paper. The solid was stirred for one hour with 500 mL of tetrahydrofuran and collected by filtration. The solid was washed with tetrahydrofuran and dried to give 7,14-dihydro-1,4,8,11-tetramethylpentacene-5,12-dione.

Preparation of 1,4,8,11-Tetramethylpentacene

A mixture of 1.0 grams of 7,14-dihydro-1,4,8,11-tetramethylpentacene-5,12-dione and 10 mL of 2-methoxyethyl ether was stirred and flushed with nitrogen for 15 minutes. To this was added 0.875 grams of sodium borohydride and stirring was continued at room temperature overnight. To the mixture was added 20 mL of 2-methoxyethyl ether and 0.75 grams of sodium borohydride and heating was continued overnight at 60° C. To the mixture was added 6.3 mL of methanol and 0.75 grams of sodium borohydride and stirring was continued for 6 hours at room temperature. To the mixture was added 15 mL of acetic acid and the mixture was stirred for one hour at room temperature. To the mixture was added 10 mL of concentrated hydrochloric acid and the mixture was heated to 60° C. for 1.5 hours. The solid was isolated by filtration, washed with water and dried to give 1,4,8,11-tetramethylpentacene.

Example 9

Preparation of 1,2,3,4,8,9,10,11-Octamethylpentacene-5,7(12H,14H)-dione

Preparation of 4,6-Bis(1,2,3,4,5-tetramethylbenzoyl)isophthalic Acid

A mixture of 73 grams of benzene-1,2,4,5-tetracarboxylic acid dianhydride (pyromellitic anhydride), 188 grams of aluminum chloride, and 465 grams of 1,2-dichloroethane was cooled to 15° C. To this was added a mixture of 90 grams of 1,2,3,4-tetramethylbenzene, 46.8 gram of N,N-diisopropylethylamine, and 183 mL of 1,2-dichloroethane over a period of 3.5 hours keeping the temperature between 15° C. and 20° C. The mixture was stirred overnight at room temperature, poured into a mixture of 225 grams of ice and 225 mL of concentrated hydrochloric acid and stirred for one hour. As much solution as possible was poured from the coagulate. The coagulate was worked up in 100 mL portions as follows. To 100 mL of the coagulate was added 600 mL of tetrahydrofuran and 300 mL of brine. The mixture was stirred and phase split. The organic phase was filtered and concentrated in vacuo. The combined residues were treated with 2500 grams of acetic acid and heated to 117° C. for 30 minutes. The mixture was cooled to room temperature and the solid was collected by filtration and washed with acetic acid and then heptane. The solid was dried to give 4,6-bis(1,2,3,4,5 tetramethylbenzoyl)isophthalic acid.

Preparation of 4,6-Bis(1,2,3,4,5-tetramethylbenzyl)isophthalic Acid

A mixture of 78.3 grams of 4,6-bis(1,2,3,4,5-tetramethylbenzoyl)isophthalic acid, 1.5 L of tetrahydrofuran, and 6.3 grams of 10% palladium on carbon (as a catalyst) was heated to 65° C. for 17 hours in an atmosphere of hydrogen at 270 kPa. The mixture was filtered through Celite™ diatomaceous earth filter agent to remove the catalyst. The filtrate was concentrated in vacuo to give 4,6-bis(1,2,3,4,5-tetramethylbenzyl)isophthalic acid.

Preparation of 1,2,3,4,8,9,10,11-Octamethylpentacene-5,7(12H,14H)-dione

To 339 grams of trifluoromethanesulfonic acid was added 48 grams of 4,6-bis(1,2,3,4,5-tetramethylbenzyl)isophthalic acid with cooling. The mixture was stirred at room temperature overnight and then poured over 600 grams of ice. The resulting solid was isolated by filtration and washed sequentially with water, saturated aqueous sodium bicarbonate, and water until the filtrate was neutral to pH paper. The solid was dried to give 1,2,3,4,8,9,10,11-octamethylpentacene-5,7(12H,14H)-dione.

Example 10

Preparation of 2,9-Di(3,5,5-trimethylhexyl)pentacene

Preparation of 3,5,5-Trimethylhexanoylbenzene

To a mixture of 143.3 grams of aluminum chloride and 400 mL of benzene was added 100 grams of 3,5,5-trimethylhexanoyl chloride over a 50 minute period at a rate such that the temperature did not exceed 35° C. When the addition was complete, the mixture was stirred at room temperature for three hours. The mixture was poured over 500 grams of ice and extracted with 400 mL of ethyl acetate. The organic phase was washed with brine, dried over magnesium sulfate, filtered and the solvent was removed in vacuo to give 3,5,5-trimethylhexanoylbenzene.

Preparation of 3,5,5-Trimethylhexylbenzene

A solution of 116.5 grams of 3,5,5-Trimethylhexanoylbenzene in 1500 mL of tetrahydrofuran with 9.9 grams of 10% palladium on carbon (as a catalyst) was stirred at 23° C. in an atmosphere of hydrogen at 275 kPa for 17 hours. The mixture was filtered through Celite™ diatomaceous earth filter agent to remove the catalyst. The filtrate was concentrated in vacuo to give 3,5,5-trimethylhexylbenzene.

Preparation of 2,5-Bis(4-(3,5,5-trimethylhexyl)benzoyl)terephthalic Acid

A mixture of 694.76 grams of aluminum chloride, 270.6 grams of benzene-1,2,4,5-tetracarboxylic acid dianhydride (pyromellitic dianhydride), and 1722.0 grams of 1,2-dichloroethane was stirred at 15° C. A mixture of 507.04 grams of (3,5,5-trimethylhexyl)benzene, 173.17 grams of N,N-diisopropylethylamine and 676.4 mL of 1,2- dichloroethane was added to the reaction over a period of 3.5 hours keeping the reaction temperature between 15° C. and 20° C. The mixture was allowed to stir overnight at room temperature and then added to 1200 g of ice and 1200 mL concentrated hydrochloric acid and stirred for 3 hours. The mixture was extracted with ethyl acetate and the ethyl acetate was washed several times with water. The organic phase was dried with magnesium sulfate and stripped to give a clear thick yellow slurry. To this was added 200 mL ethyl acetate followed by 600 mL of heptane and stirred for 15 minutes. The solid was collected by filtration to give 2,5-bis(4-(3,5,5-trimethylhexyl)benzoyl)terephthalic acid.

Preparation of 2,5-Bis(3,5,5-trimethylhexylbenzyl)terephthalic Acid

A mixture containing 20.0 grams of 2,5-bis[4-(3,5,5-trimethylhexyl)benzoyl]terephthalic acid in 1500 mL of tetrahydrofuran (THF) and 1.4 grams of 10% palladium on carbon (as a catalyst) was heated to 90° C. in an atmosphere of hydrogen at 620 kPa and 90° C. for 17 hours. The mixture was filtered through Celite™ diatomaceous earth filter agent to remove the catalyst. The filtrate was concentrated in vacuo to give 2,5-bis[4-(3,5,5-trimethylhexyl)benzyl]terephthalic acid.

Preparation of 7,14-Dihydro-3,10-(3,5,5-trimethylhexyl)pentacene-5,12-dione

A mixture of 16.8 grams of trifluoromethanesulfonic acid and 3.0 grams of 2,5-bis(3,5,5-trimethylhexy)terephthalic acid was stirred for 30 minutes. The reaction temperature was about 30° C. during the addition. The reaction mixture was maintained at 40° C. for 3 hours. The reaction mixture was cooled and poured over ice, filtered and washed with water until the filtrate had a pH of greater than 4. The residue was air dried and then stirred with 200 mL of ethyl acetate. This mixture was filtered and the filtrate was concentrated to give 7,14-Dihydro-3,10-(3,5,5-trimethylhexyl)pentacene-5,12-dione.

Preparation of 2,9-Di(3,5,5-trimethylhexyl)pentacene

To 1 gram of 7,14-dihydro-3,10-(3,5,5-trimethylhexyl)pentacene-5,12-dione in 20 mL of 2-methoxyethyl ether was added 0.56 grams of sodium borohydride. The mixture was stirred and flushed with nitrogen at 100° C. for 2 hours and quenched with 10 mL of methanol at 60° C. over 30 minutes, followed by drop-wise addition of 10 mL of acetic acid and then 5 mL of concentrated hydrochloric acid. The reaction mixture was cooled to room temperature and filtered. A resulting blue solid residue was washed with acetic acid, water, methanol and then finally with acetone and dried. This material was heated in approximately 10 mL of n-butylbenzene and filtered to give 2,9-Di(3,5,5-trimethylhexyl)pentacene.

Example 11

Preparation of 2,9-Di(2-ethylhexyl)pentacene

Preparation of 3,5,5-Trimethylhexanoylbenzene

A mixture of 143.4 grams of aluminum chloride and 351.6 grams of benzene was stirred at room temperature while 100 grams of 3,5,5-trimethylhexanoyl chloride was added to the reaction keeping the reaction temperature at approximately 35° C. over a period of 1.5 hours. The mixture was then stirred for 3 hours. The reaction mixture was poured into 500 grams of ice and stirred until all the ice dissolved. Water was added with cooling to give a homogenous mixture followed by extraction with 400 mL of ethyl acetate. The organic phase was washed with brine, dried with anhydrous magnesium sulfate and stripped to dryness to give 3,5,5-Trimethylhexanoylbenzene.

Preparation of 2-Ethylhexylbenzene

A solution of 313.9 grams of 2-ethylhexanoylbenzene in 500 mL of acetic acid with 11.4 grams of 10% palladium on carbon (as a catalyst) was stirred at 110° C. in an atmosphere of hydrogen at 414 kPa for 34 hours. The mixture was filtered through Celite™ diatomaceous earth filter agent to remove the catalyst. The filtrate was concentrated in vacuo to give 2-ethylhexylbenzene.

Preparation of 2,5-Bis(4-(2-ethylhexyl)benzoyl)terephthalic Acid

A mixture of 215.39 grams of aluminum chloride, 83.89 grams of benzene-1,2,4,5-tetracarboxylic acid dianhydride (pyromellitic dianhydride), and 533.85 grams of 1,2-dichloroethane was stirred at 15° C. to 16° C. To this mixture was added a solution of 183 grams of (2-ethylhexyl)benzene and 53.685 grams of N,N-diisopropylethylamine in 198 mL of 1,2-dichloroethane over a period of 3.5 hours keeping the reaction temperature between 15° C. and 20° C. The mixture was stirred overnight at room temperature and then added to 400 g of ice and 400 mL concentrated hydrochloric acid. This mixture was stirred for 1 hour. The mixture was extracted with ethyl acetate. The organic phase was washed with water and brine, dried, and stripped. The resulting solid was stirred with 700 mL ethyl acetate for 10 minutes and 2000 mL of heptane was added. This mixture was stirred for 15 minutes and then filtered. The residue was washed with a mixture of 275 mL ethylacetate/825 mL heptane and air dried to give 2,5-Bis(4-(2-ethylhexyl)benzoyl)terephthalic acid.

Preparation of 2,5-Bis(4-(2-ethylhexyl)benzyl)terephthalic Acid

A mixture containing 20.0 grams of 2,5-bis(4-(2-ethylhexyl)benzoyl)terephthalic acid in 1500 mL of THF and 2.9 grams of 10% palladium on carbon (as a catalyst) was heated to 65° C. in an atmosphere of hydrogen at 275 kPa for 17 hours. The mixture was filtered through Celite™ diatomaceous earth filter agent to remove the catalyst. The filtrate was concentrated in vacuo to give 2,5-Bis(4-(2-ethylhexyl)benzyl)terephthalic acid.

Preparation of 3,10-Di(2-ethylhexyl)-7,14-dihydropentacene-5,12-dione

A mixture of 35 grams of 2,5-bis(2-ethylhexy)terephthalic acid and 121 mL of trifluoromethanesulfonic acid was allowed to exotherm to 51° C. The mixture was stirred for a total of 6.5 hours. The mixture was poured over 500 mL of ice and stirred until it was completely mixed. The precipitate was collected and washed with five liters of water until the filtrate had a pH of 4.0. The solid was air dried to give 3,10-Di(2-ethylhexyl)-7,14-dihydropentacene-5,12-dione.

Preparation of 2,9-Di(2-ethylhexyl)pentacene

A method essentially as described above in Example in 10 (Preparation of 2,9-Di(3,5,5-trimethylhexyl)pentacene) is used to prepare 2,9-Di(2-ethylhexyl)pentacene from 3,10-Di(2-ethylhexyl)-7,14-dihydropentacene-5,12-dione Example 12

Preparation Process for Pentacene Including Step of Using Trifluoromethanesulfonic Acid Preparation of 2,5-Dibenzylterephthalic Acid and 4,6-Dibenzylisophthalic Acid To a mixture of 100 grams of 2,5-bis-benzoylterephthalic acid and 4,6-dibenzoylisophthalic acid was added 1.5 L of tetrahydrofuran and 10.4 grams of 10% palladium on carbon (as a catalyst). This mixture was heated to 65° C. for 17 hours in an atmosphere of hydrogen at 270 kPa. The resulting mixture was filtered through Celite™ diatomaceous earth filter agent to remove the catalyst. The filtrate was concentrated in vacuo to give a mixture of 2,5-dibenzylterephthalic acid and 4,6-dibenzylisophthalic acid.
Preparation of 7,14-Dihydropentacene-5,12-dione and Pentacene-5,7(12H,14H)-dione To 20 mL of trifluoromethanesulfonic acid cooled to 7° C. was added 3.0 grams of a mixture of 2,5-dibenzylterephthalic acid and 4,6-dibenzylisophthalic acid. The mixture was stirred at room temperature for three hours and poured over 50 grams of ice. The resulting solid was isolated by filtration and washed sequentially with water, saturated aqueous sodium bicarbonate, and water until the filtrate was neutral to pH paper. The solid was dried to give a mixture of 7,14-dihydropentacene-5,12-dione and pentacene-5,7(12H,14H)-dione.
Preparation of Pentacene A mixture of 1.0 gram of 7,14-dihydropentacene-5,12-dione and pentacene-5,7(12H,14H)-dione, and 10 mL of 2-methoxyethyl ether was stirred and flushed with nitrogen for 15 minutes. To this was added 1.03 grams of sodium borohydride and stirring was continued at room temperature overnight. To the mixture was added 10 mL of 2-methoxyethyl ether and 6.3 mL of methanol and stirring was continued for 1.5 hours at room temperature. To the mixture was added 15 mL of acetic acid and 10 mL of concentrated hydrochloric acid. The mixture was stirred for one hour at room temperature and heated to 60° C. for one hour. To the mixture was added 50 mL of water, and the resulting solid was isolated by filtration and washed with water. The solid was washed with tetrahydrofuran until a pale filtrate resulted. The solid was washed with heptane and dried to give pentacene.

Example 13

Preparation Process for Pentacene Using Aluminum tri(sec-butoxide)

To a mixture of 1.0 gram of pentacene-5,7,12,14-tetrone in 100 mL of cyclohexanol was added 7.3 grams of aluminum tri(sec-butoxide). The reaction mixture was heated to 145° C. for 66 hours. The reaction mixture was cooled to room temperature and placed in a centrifuge. A dark solid was separated and washed 3 times with cyclohexanol followed by centrifugation. The residue was washed with acetone, isolated on a filter flask, and air dried to give pentacene Example 14

Preparation Process for 2,9-Difluoropentacene Using Aluminum tri(sec-butoxide)

To a mixture of 0.5 grams of 2,9-difluoropentacene-5,7, 12,14-tetrone and 20 mL of cyclohexanol in a flask was added 3.640 grams of aluminum tri(sec-butoxide). The mixture was heated at 100° C. for approximately 12 hours and a blue solid deposited on the sides of the flask. The reaction mixture was centrifuged and the blue solid residue was washed with cyclohexanol, centrifuged twice, and then washed with acetone and collected by filtration. This solid was washed with 50% concentrated HCl and the resulting mixture was centrifuged to give a blue solid. This solid was washed with THF and collected by centrifugation to give 2,9-difluoropentacene.

Example 15

Preparation Process for 2,9-Dimethylpentacene Using Aluminum tri(sec-butoxide)

To a 500 mL three necked round bottom flask with a thermometer, and a distillation head was added 32.76 grams of aluminum tri(sec-butoxide) and 200 mLs of cyclohexanol. To this was added 9 grams 3,10-Dimethylpentacene-5,12-dione. The reaction mixture was heated to 145° C. At 140° C., 8.7 grams of a distillate was collected. The reaction mixture was heated at 140° C. for 43 hours and cooled to room temperature. A solid was isolated by centrifugation. The supernate liquid was poured off and the solid was slurried with 140 mLs of 1N HCl and isolated on a Buchner funnel. The solid was slurried three times with 100 mLs each 1N HCl and the solvent was poured off each time. The solid was slurried three times with 100 mLs of acetone and isolated by filtration. The solid was slurried three times with 100 mLs of THF and isolated by filtration. The residue was air dried to give 2,9-dimethylpentacene.

Example 16

Preparation Process for 2,9-Dihexylpentacene Using Aluminum tri(sec-butoxide)

A mixture of 5.69 grams of aluminum tri(sec-butoxide) and 49.1 mLs of cyclohexanol was made. To this was added 2.21 grams 3,10-Dihexylpentacene-5,12-dione. The reaction mixture was heated to 145° C. for 24 hours. The mixture was cooled to room temperature and the solid isolated by centrifugation. The solid was stirred with 40 mLs of cyclohexanol and centrifuged two times. The solid was collected by filtration and washed with THF to give 2,9-dihexylpentacene.

Example 17

Preparation Process for 2,9-Dihexylpentacene Using Aluminum tri(sec-butoxide)

A mixture of 1.0 grams of 3,10-dihexylpentacene-5,12-dione and 2.5 grams of aluminum tri(sec-butoxide) in 50 mL of mesitylene was heated to 155° C. for 2 days and cooled. The reaction mixture was filtered and the residue washed with concentrated HCl to give 2,9-dihexylpentacene.

Example 18

Preparation Process for Benzophenones Using Trifluoromethanesulfonic Acid

As listed in Table 1, a solution of 1.0 gram of a diarylcarboxylic acid was dissolved in 10 mL of trifluoromethanesulfonic acid and heated for the amount of time indicated. The reaction mixture was cooled and poured over ice. For liquid products, the aqueous layer was extracted with ethyl acetate and the organic layer was washed with water followed by saturated aqueous sodium bicarbonate solution. The organic layer was dried and concentrated to give the product. For solid products, the solid was collected by filtration and the residue was washed with water and air dried to give the product.

TABLE 1

| Entry | Starting Material | Reaction Temp | Reaction Time | Product |
| --- | --- | --- | --- | --- |
| 1 | 2-(phenylthiomethyl)benzoic acid | 60° C. | 4 days | dibenzo[b,e]thiepin-11(6H)-one |
| 2 | 2-(2-phenylethyl)benzoic acid | 23° C. | 10 minutes | 10,11-dihydro-5H-dibenzo[a,d]cyclohepten-5-one |
| 3 | 2,2'-iminodibenzoic acid | 23° C. | 24 hours | 9-oxo-9,10-dihydroacridine-4-carboxylic acid |
| 4 | biphenyl-2,2'-dicarboxylic acid | 23° C. | 24 hours | 9-oxo-9H-fluorene-1-carboxylic acid |
| 5 | biphenyl-2-carboxylic acid | 23° C. | 2.5 hours | 9H-fluoren-9-one |
| 6* | fluorinated diaroyl dicarboxylic acid | 150° C. | 18 hours | difluoropentacenetetraone |
| 7 | diaroyl dicarboxylic acid | 155° C. | 15 hours | pentacenetetraone |

*The reaction mixture for Entry 6 contained 3 equivalents of trifluoroacetic anhydride.

Example 19

Preparation Process for Fluorenone (9H-Fluoren-9-one) Using Trifluoromethanesulfonic Acid To 1.0 grams of 2-biphenylcarboxylic acid was added 3 mL of trifluoromethanesulfonic acid. The sample was maintained at room temperature for 2.5 hours The mixture was poured over ice-water and extracted with ethyl acetate. The organic phase was washed with a saturated aqueous sodium bicarbonate solution until the aqueous phase was basic. The aqueous phase was separated. The organic phase was washed with water, dried over magnesium sulfate, and concentrated in vacuo to give 9H-fluoren-9-one.

Comparative Example C1

Combining 2,5-Dibenzylterephthalic Acid, 4,6-Dibenzylisophthalic Acid, and Sulfuric Acid To an 80 mg mixture of 2,5-dibenzylterephthalic acid and 4,6-dibenzylisophthalic acid was added 3 grams of concentrated sulfuric acid. The resulting mixture was stirred at room temperature. After three hours the mixture contained an impurity that was not present in the reaction mixture containing trifluoromethanesulfonic acid and dibenzylphthalic acids.

Comparative Example C2

Combining 2,5-Bis(4-methylbenzyl)terephthalic Acid and Polyphosphoric Acid

A mixture of 0.2 grams of 2,5-bis(4-methylbenzyl) terephthalic acid and 4 mL of polyphosphoric acid was heated to 80° C. The solid did not dissolve completely, and the mixture remained colorless. The viscous mixture was heated for 2 hours at 80° C. The mixture was cooled to room temperature and added to water. The solid was collected by filtration, washed with hexane and dried to give recovered starting material.

Comparative Example C3

Combining 2,5-Bis(4-methylbenzyl)terephthalic Acid and Sulfuric Acid with Short Reaction Time A mixture of 0.1 grams of 2,5-bis(4-methylbenzyl) terephthalic acid and 2 mL concentrated sulfuric acid was stirred at room temperature for 34 minutes. The mixture was poured over ice and the solid was collected by filtration to give recovered starting material.

Comparative Example C4

Combining 2,5-Bis(4-methylbenzyl)terephthalic Acid and Sulfuric Acid with Long Reaction Time To an 80 mg sample of 2,5-bis(4-methylbenzyl) terephthalic acid was added 3 grams of concentrated sulfuric acid. The mixture was stirred at room temperature. After remaining at room temperature for 24 hours the reaction mixture contained approximately 20% of 7,14-dihydro-3,10-dimethylpentacene-5,12-dione, 40% of 6-methyl-3-(4-methylbenzyl)-10-oxo-9,10-dihydroanthracene-2-carboxylic acid (the mono-cyclized intermediate) and 40% of 2,5-bis(4-methylbenzyl)terephthalic acid (starting material).

Comparative Example C5

Combining 2,5-Bis(4-nonylbenzyl)terephthalic Acid and Sulfuric Acid

A mixture of 0.5 grams of 2,5-bis(4-nonylbenzyl) terephthalic acid in 10 mL of concentrated sulfuric acid was heated to 65° C. After one hour at 65° C. an aliquot of the mixture was quenched and only starting material was recovered. No 7,14-dihydro-3,10-dinonylpentacene-5,12-dione was formed after 24 hours at 65° C.

The complete disclosures of the publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A process for preparing pentacene compounds comprising the step of cyclizing at least one substituted bis (benzyl)phthalic acid to form the corresponding substituted pentacenedione by using an acid composition comprising trifluoromethanesulfonic acid, said substituted bis(benzyl) phthalic acid being selected from those represented by the following general formulas:

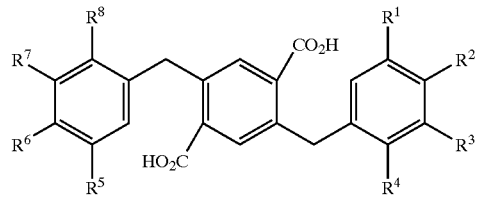

Formula 1(a)

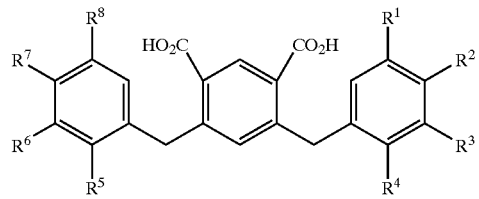

Formula 1(b)

wherein each R group is independently selected from the group consisting of electron-donating groups, halogen atoms, hydrogen atoms, and combinations thereof.

2. The process of claim 1 wherein each said R group is independently selected from the group consisting of alkyl groups, alkoxy groups, thioalkoxy groups, halogen atoms, hydrogen atoms, and combinations thereof.

3. The process of claim 2 wherein each said R group is independently selected from the group consisting of alkyl groups, alkoxy groups, hydrogen atoms, and combinations thereof.

4. The process of claim 3 wherein each said R group is independently selected from the group consisting of alkyl groups and hydrogen atoms.

5. The process of claim 4 wherein each said R group is independently selected from the group consisting of methyl, n-hexyl, n-nonyl, n-dodecyl, sec-butyl, 3,5,5-trimethylhexyl, 2-ethylhexyl, and hydrogen.

6. The process of claim 1 wherein said $R^2$ and said $R^6$ of said Formula 1(a) are independently selected from the group consisting of electron-donating groups, halogen atoms, and combinations thereof; and said $R^1$, $R^3$, $R^4$, $R^5$, $R^7$, and $R^8$ are hydrogen atoms.

7. The process of claim 1 wherein said $R^2$ and said $R^7$ of said Formula 1(b) are independently selected from the group consisting of electron-donating groups, halogen atoms, and combinations thereof; and said $R^1$, $R^3$, $R^4$, $R^5$, $R^6$, and $R^8$ are hydrogen atoms.

8. The process of claim 6 wherein said electron-donating group is selected from the group consisting of alkyl groups, alkoxy groups, and thioalkoxy groups.

9. The process of claim 7 wherein said electron-donating group is selected from the group consisting of alkyl groups, alkoxy groups, and thioalkoxy groups.

10. The process of claim 8 wherein said $R^2$ and said $R^6$ are independently selected from the group consisting of alkyl groups, alkoxy groups, and combinations thereof.

11. The process of claim 9 wherein said $R^2$ and said $R^7$ are independently selected from the group consisting of alkyl groups, alkoxy groups, and combinations thereof.

12. The process of claim 10 wherein said $R^2$ and said $R^6$ are independently alkyl.

13. The process of claim 11 wherein said $R^2$ and said $R^7$ are independently alkyl.

14. The process of claim 12 wherein said $R^2$ and said $R^6$ are independently selected from the group consisting of methyl, n-hexyl, n-nonyl, n-dodecyl, sec-butyl, 3,5,5-trimethylhexyl, 2-ethylhexyl, and hydrogen.

15. The process of claim 13 wherein said $R^2$ and said $R^7$ are independently selected from the group consisting of methyl, n-hexyl, n-nonyl, n-dodecyl, sec-butyl, 3,5,5-trimethylhexyl, 2-ethylhexyl, and hydrogen.

16. The process of claim 1 further comprising the step of reducing said substituted pentacenedione to the corresponding substituted pentacenediol.

17. The process of claim 16 further comprising the step of dehydrating said substituted pentacenediol to the corresponding substituted pentacene.

18. Substituted bis(benzyl)phthalic acid compounds represented by the following general formulas:

Formula 1(a)

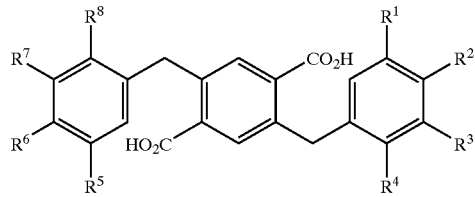

Formula 1(b)

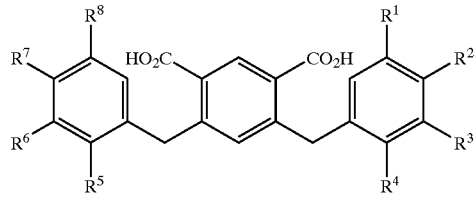

wherein each R group is independently selected from the group consisting of electron-donating groups, halogen atoms, hydrogen atoms, and monovalent combinations therefore.

19. The compounds of claim 18 wherein each said R group is independently selected from the group consisting of alkyl groups and hydrogen atoms.

20. Substituted bis(benzoyl)phthalic acid compounds represented by the following general formulas:

Formula 4(a)

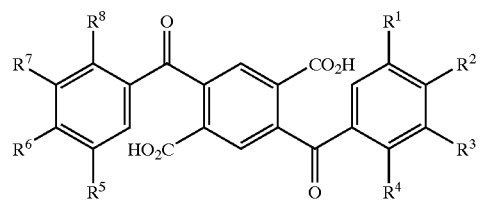

Formula 4(b)

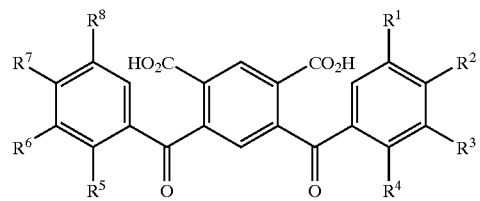

wherein each R group is independently selected from the group consisting of hydrogen atoms and alkyl groups having at least two carbon atoms.

* * * * *

UNITED STATES PATENT AND TRADEMARK OFFICE
CERTIFICATE OF CORRECTION

PATENT NO. : 6,974,877 B2  Page 1 of 2
APPLICATION NO. : 10/256489
DATED : December 13, 2005
INVENTOR(S) : Dennis E. Vogel It is certified that error appears in the above-identified patent and that said Letters Patent is hereby corrected as shown below:

On the Title Page,
Item (56), References Cited, OTHER PUBLICATIONS, Col. 1,
Line 3, after "abstract." insert -- ) --.
Item (56), References Cited, OTHER PUBLICATIONS, Col. 1,
Line 4, delete "et al," and insert in place thereof -- et al., --.
Item (56), References Cited, OTHER PUBLICATIONS, Page 2, Col. 1,
Line 27, delete "Serie" and insert in place thereof -- Series --.
Item (56), References Cited, OTHER PUBLICATIONS, Page 2, Col. 2,
Lines 14-15, after "anthracene]$^1$" delete "). Its" and insert in place therefor -- , its --.
Item (56), References Cited, OTHER PUBLICATIONS, Page 2, Col. 2,
Line 16, after "(1929)" delete "." and insert in place thereof -- , --.

Column 20,
Line 46, after "R$^6$" insert -- , --.

Column 26,
Line 4, delete

"  " and insert in place thereof

-- 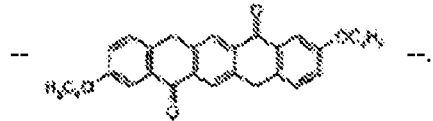 --.

UNITED STATES PATENT AND TRADEMARK OFFICE
CERTIFICATE OF CORRECTION

PATENT NO. : 6,974,877 B2
APPLICATION NO. : 10/256489
DATED : December 13, 2005
INVENTOR(S) : Dennis E. Vogel It is certified that error appears in the above-identified patent and that said Letters Patent is hereby corrected as shown below:

Columns 35-36,
Lines 8-10 (Structures), before "It is possible", delete

" 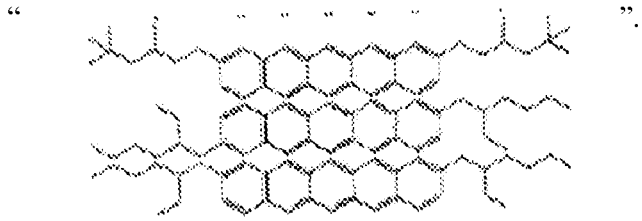 ".

Column 56,
Line 4, delete "therefore." and insert in place thereof -- thereof. --.

Signed and Sealed this

Fifth Day of August, 2008

JON W. DUDAS
*Director of the United States Patent and Trademark Office*